United States Patent [19]

Szita et al.

[11] Patent Number: 5,612,084
[45] Date of Patent: Mar. 18, 1997

[54] AMINOPLAST-ANCHORED ULTRAVIOLET LIGHT STABILIZERS

[75] Inventors: Jeno G. Szita, Norwalk; Paul S. Waterman, Shelton, both of Conn.

[73] Assignee: Cytec Technology Corp., Wilmington, Del.

[21] Appl. No.: 448,161

[22] Filed: May 23, 1995

Related U.S. Application Data

[62] Division of Ser. No. 998,099, Dec. 29, 1992.

[51] Int. Cl.$^6$ ..................................................... B05D 3/02
[52] U.S. Cl. ..................... 427/160; 427/388.2; 427/393; 427/393.5; 427/397
[58] Field of Search .................................. 427/160, 388.2, 427/393, 393.5, 397

[56] References Cited

U.S. PATENT DOCUMENTS

| | | | |
|---|---|---|---|
| 3,316,208 | 4/1967 | Lee et al. | 260/45.8 |
| 3,399,173 | 8/1968 | Heller et al. | 260/47 |
| 3,535,318 | 10/1970 | Oppelt et al. | 260/249.6 |
| 3,595,602 | 7/1971 | Oppelt et al. | 8/74 |
| 4,197,392 | 4/1980 | Moore | 528/127 |
| 4,233,430 | 11/1980 | Jacquet et al. | 526/259 |
| 4,319,016 | 3/1982 | Kurobe et al. | 528/127 |
| 4,355,071 | 10/1982 | Chang | 428/334 |
| 4,418,000 | 11/1983 | Zannucci et al. | 252/403 |
| 4,418,001 | 11/1983 | Zannucci et al. | 252/403 |
| 4,418,002 | 11/1983 | Zannucci et al. | 252/403 |
| 4,612,358 | 9/1986 | Besecke et al. | 526/259 |
| 4,652,656 | 3/1987 | Besecke et al. | 548/261 |
| 4,913,974 | 4/1990 | Moore et al. | 428/480 |

FOREIGN PATENT DOCUMENTS

| | | |
|---|---|---|
| 1065991 | 11/1979 | Canada . |
| 1272729 | 8/1990 | Canada . |
| 0191582 | 8/1986 | European Pat. Off. . |
| 49-063681 | 6/1974 | Japan . |
| 54-014437 | 2/1979 | Japan . |
| 63-205334 | 8/1988 | Japan . |
| 1287160 | 11/1989 | Japan . |
| 01287160 | 11/1989 | Japan . |
| 1169859 | 11/1969 | United Kingdom . |

OTHER PUBLICATIONS

"Facile Syntheses of 2, 4–Dihydroxybenzophenone Derivatives With Polymerizable Vinyl Groups," Journal of Polymer Sciences, Polymer Letters Edition, vol. 15, No. 11, pp. 675–677 (1977).

R.O.C. Norman, "Electrophilic Aromatic Substitution" in Principles of Organic Synthesis, 2nd ed., Chapman and Hall, London, pp. 370–377 (1978).

M. Minagawa, "New Developments in Polymer Stabilization," Polymer Degradation and Stability, vol. 25, pp. 121–141 (1989).

European Search Report for European Appln. 93121013.2, dated Apr. 29, 1994.

*Primary Examiner*—Shrive Beck
*Assistant Examiner*—Erma Cameron
*Attorney, Agent, or Firm*—Bart E. Lerman; Claire M. Schultz; Michael J. Kelly

[57] ABSTRACT

Novel aminoplast anchored UV stabilizers are provided. Compared to unanchored stabilizers, the anchored stabilizers disclosed herein have increased compatibility with coating resins and have reduced volatility due to higher molecular weights resulting from anchoring. A process for preparing the anchored stabilizers by the reaction of unanchored stabilizers with alkoxymethylated aminoplasts in a sulfuric acid medium is also provided. The unanchored stabilizers include 2-(2-hydroxyaryl)benzotriazoles, 2-hydroxybenzophenones, 2-(2-hydroxyaryl)-4,6-diaryl-1,3,5-triazines, salicylic acid derivatives, 2-hydroxyoxanilides, and blocked derivatives thereof as well as mixtures of two or more stabilizers. The aminoplasts include alkoxymethylated derivatives of glycolurils, melamines, and benzoguanamines.

54 Claims, No Drawings

AMINOPLAST-ANCHORED ULTRAVIOLET LIGHT STABILIZERS

This is a divisional of co-pending application Ser. No. 07/998,099, filed Dec. 29, 1992.

FIELD OF THE INVENTION

This invention relates to the preparation and use of novel aminoplast-anchored phenolic ultraviolet light stabilizers.

BACKGROUND OF THE INVENTION

Stabilization of polymers by incorporation of ultraviolet light stabilizers in polymer films, coatings, fibers, and molded articles to provide protection against the degrading action of light, moisture, or oxygen has been an active area of work in recent years. However, deficiencies such as volatility and generally poor retention of existing stabilizers within a polymer matrix still remain largely unsolved. For example, attempts to reduce volatility by using higher molecular weight oligomers and polymers have generally resulted in a decreased retention of the stabilizer due to incompatibility. Extractibility and migration of the stabilizer to the surface and eventually loss as a result of incompatibility or low molecular weight are still serious problems plaguing the plastics industry.

Limited attempts to increase the molecular weight of the stabilizer without introducing incompatibility by using anchor groups have been made in the past without great success. Among the anchor groups used for supporting stabilizers, triazines have received some attention. U.S. Pat. No. 4,319,016 describes an ultraviolet absorbing material which is the reaction product of (a) a hydroxyphenyl ultraviolet light absorbing compound, (b) formaldehyde, and (c) an amino-group containing compound, such as melamine. It is stated therein that if the hydroxyphenyl compound is present in amounts greater than 0.5 mole per mole of melamine, the amount of unreacted hydroxyphenyl compound frequently increases and the compatibility of the resulting compound with a resin or solvent tends to be reduced. The reaction product obtained by the method described therein is not described in the patent.

U.S. Pat. Nos. 3,535,318; 3,595,602; 4,418,000; 4,418,001; and 4,418,002; and Japense Patent No. 01-287160 describe reaction products obtained by reacting hydroxy group-containing ultraviolet absorbers with alkoxymethyl-group containing aminoplasts. The attachment of the ultraviolet absorbing group of the aminoplast anchor, however, is always through a weak carbon-oxygen bond between the bridging methylene group of the aminoplast and the hydroxy group of the ultraviolet light absorbing component.

U.S. Pat. Nos. 3,316,208; 4,197,392; and 4,913,974; and Canadian Patent No. 1,065,991 describe acid curable compositions containing ultraviolet light absorbers and alkoxymethyl group-containing aminoplast. Despite the presence of acids, there is no suggestion in these references of any reaction between the absorber component and the aminoplast component of said curable compositions.

U.S. Pat. Nos. 4,612,358; 4,652,656; and 3,399,173; Japense Patent No. 63-205334; and a review article in "Caoutchoucs et Plastiques", No. 575, November 1977 describe ultraviolet light absorbing polymerizable monomers and polymers thereof. An article in "Polymer Degradation and Stability," Vol. 25, pages 121–141 (1989) entitled "New Developments in Polymer Stabilization" describes the effects of molecular weight of stabilizers on performance.

U.S. Pat. No. 4,355,071 describes clear coat/color coat finishes in which stabilizers are able to migrate across the interface. An article in Journal of Polymer Science, Polymer Letters, Volume 15, Number 11, pages 675 to 677 (1977) and U.S. Pat. Nos. 4,612,358 and 4,652,656 disclose the use of 95 to 98% sulfuric acid in the preparation of polymerizable, benzophenone and benzotriazole type stabilizers. U.S. Pat. No. 4,233,430 similarly discloses the use of sulfuric acid in the preparation of related polymers.

The object of this invention is to provide novel aminoplast-anchored blocked and unblocked phenolic stabilizers.

Another object of this invention is to provide a process for the preparation of the novel stabilizers of the invention.

It is yet another object of this invention to provide curable compositions containing the novel stabilizers of the invention and also provide stabilized cured compositions obtained by curing said curable compositions.

It is yet another object of this invention to provide an improved method of stabilizing polymers wherein the improvement comprises adding to said polymers the novel stabilizers of the invention.

SUMMARY OF THE INVENTION

This invention is a novel composition of matter comprising blocked or unblocked, monomeric and oligomeric aminoplast-anchored phenolic ultraviolet light stabilizer having at least 0.5 mole of phenolic stabilizer groups per mole of aminoplast anchor.

This invention is also a process for preparing the novel stabilizers of the invention.

This invention is also a curable composition containing the novel stabilizers of the invention.

This invention is also a cured composition containing the novel stabilizers of the invention.

This invention is also an improved method of stabilizing polymers wherein the improvement comprises adding to said polymers the novel stabilizers of the invention.

The advantages of the anchored stabilizers of this invention over their unanchored precursors include generally higher compatibility with polymers and resins, and generally lower volatility due to higher molecular weights.

DETAILED DESCRIPTION OF THE INVENTION

The novel composition of this invention is an amino resin anchor molecule having pendant on it one or more phenolic stabilizer groups. The broad discovery of this invention is that chemically combining amino resins and phenolic stabilizers into a single compound or oligomer yields a composition of matter that unexpectedly retains the stabilizing effect of the phenolic stabilizer, permits combinations of stabilizers at the molecular level, and gains advantageous properties from the amino resins such as enhanced compatibility and reduced volatility.

For example, the gain in molecular weight by the chemical combination of the stabilizer and amino resin generally makes the novel compositions less volatile in polymeric compositions, thereby minimizing loss and toxicity. The gain in solubility in resins generally makes the compositions more compatible with the matrix, thereby minimizing extractibility and loss.

The present invention provides a wide variety anchored stabilizers because of the ability to change any of the following variables:

1. The type of amino resin anchors.
2. The type of stabilizer reactant(s).
3. Degree of reaction of (1.) and (2.) (extent of substitution).

The following sections of this Detailed Description will illustrate useful types of amino resins for formation of the novel compounds of the invention. By way of example, specific use of the following amino resin types is set forth below:

1. glycoluril type resins
2. melamine type resins
3. guanamine type resins

The following sections will also illustrate useful types of phenolic stabilizers for formation of the novel compounds of the invention. By way of example, specific use of the following chemical classes of stabilizers is set forth below:

1. benzotriazoles
2. benzophenones
3. aryltriazines
4. salicylic acid derivatives
5. oxanilides It should specifically be noted that more than one type of stabilizer (viz., a mixture of stabilizers) may be placed on an amino resin anchor molecule. This provides a novel product with a wide spectral response having particular utility for ultraviolet and actinic light induced degradation.

The following sections will also illustrate the variety of novel compounds resulting from the degree of reaction between the amino resin anchor and the stabilizer.

The amino resin anchor may be fully or partially reacted with the stabilizer, creating three categories of novel compounds as follows:

1. Amino resin/stabilizer compounds wherein the stabilizer is on the average reacted with substantially all of the available reactive sites on the amino resin. This results in a novel compound having a high degree of stabilizer activity and reduced volatility.
2. Amino resin/stabilizer compounds wherein the stabilizer is on the average reacted with all but one of the available reactive sites on the amino resin. This results in a novel compound which can chemically combine with plastics which are known to react with amino resins to give a pendant group with stabilizer functionality.
3. Amino resin/stabilizer compounds wherein the stabilizer is on the average reacted so as to leave two or more available reactive sites on the amino resin. This results in a novel compound which can chemically act as a crosslinking agent. Such novel crosslinking agents also act as stabilizers.

The word "stabilizer" is used herein to mean a group derived from a phenolic compound that has known utility to prevent degradation by environmental forces, inclusive of ultraviolet light, actinic radiation, oxidation, moisture, atmospheric pollutants, and combinations thereof.

The novel aminoplast-anchored ultraviolet (UV) stabilizers of this invention are monomeric or oligomeric aminoplasts having more than 0.5 mole of pendently attached phenolic light stabilizer groups per mole of aminoplast. The phenolic light stabilizer moiety may be any conventional UV stabilizer, such as one selected from the group consisting of:

(1) 2-(2-hydroxyaryl)benzotriazoles,
(2) 2-hydroxybenzophenones,
(3) 2-(2-hydroxyaryl)-4,6-diaryl-1,3,5-triazines,
(4) salicylic acid derivatives,
(5) 2-hydroxyoxanilides,
(6) blocked derivatives of (1) to (5), wherein the phenolic OH group is blocked with a suitable blocking group, and
(7) mixtures of (1) to (6).

The novel aminoplast-anchored phenolic UV stabilizers of the invention have a monomeric or oligomeric aminoplast nucleus which has more than 0.5 mole of phenolic UV stabilizer groups per mole of aminoplast pendently attached thereto with methylene bridges. Generically, the novel stabilizers of this invention may be represented by the following formula:

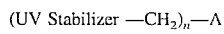
(UV Stabilizer —CH$_2$)$_n$—A wherein

A is a monomeric or oligomeric aminoplast anchor molecule serving as a nucleus for supporting the pendently attached phenolic UV stabilizer groups; and n is a number having an average minimum value greater than 0.5 and a maximum value equal to the number of stabilizer-reactive groups present on the aminoplast anchor.

The stabilizer-reactive group in the aminoplast anchor molecule is typically an alkoxymethyl group, but other reactive groups, such as hydroxy, acyloxy, halo, mercapto, sulfonyl, sulfonate, sulfate, phosphate, dialkylsulfonium, trialkylammonium, and the like may also be used.

The unblocked or hydroxyl-blocked novel aminoplast anchored phenolic stabilizers of the invention may also be represented by the following formula:

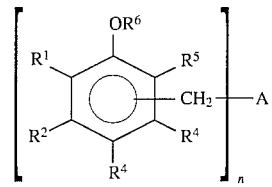

wherein

A is an m functional monomeric or oligomeric aminoplast anchor molecule to which n phenolic rings are attached through n methylene bridges, said bridges replacing R$^2$, R$^3$, R$^4$, or R$^5$ groups on said phenolic rings;

R$^1$ is a group which, together with the phenolic ring, comprises a phenolic UV stabilizer;

R$^2$, R$^3$, R$^4$, and R$^5$ are substituents selected from the group consisting of hydrogen, alkyl, aryl, aralkyl, hydroxy, alkoxy, and oxygenated alkyl groups; and R$^6$ is hydrogen or a blocking group selected from the group consisting of alkyl, acyl, aminocarbonyl, and silyl groups.

By m functional aminoplast, it is meant that there are m reactive groups on the aminoplast anchor molecule each of which can potentially react with a light stabilizer group to form the aminoplast-anchored light stabilzers of this invention.

AMINOPLAST ANCHORS

The aminoplast anchor molecules of this invention are aminoplast crosslinkers commonly used in coatings, moldings, and adhesives. The term "aminoplast" is defined herein as a class of resins which may be prepared by the reaction of an amino group-containing compound and an aldehyde.

The reaction product of amino group-containing compounds and aldehyde is often reacted further with an alcohol to produce partially or fully alkylated derivatives. These derivatives are included in the "aminoplast" definition given above. The term "aminoplast" as used in the context of this invention comprises typically a polyfunctional amino resin, and may be monomeric or oligomeric. For example, in the preparation of aminoplasts from amino group-containing compounds and aldehydes and subsequent alkylation, dimeric and oligomeric products resulting from self-condensation reaction are often obtained. These oligomeric self-condensation products are included in the "aminoplast" definition given above.

By way of example, the aminoplast anchors A of this invention include the groups represented by the following formulae (1)–(17):

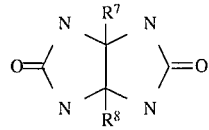
(1)

wherein $R^7$ and $R^8$ are independently, hydrogen, alkyl or aryl groups of 1 to 20 carbon atoms;

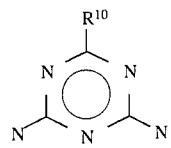
(2)

wherein $R^{10}$ is an aliphatic or cycloaliphatic alkyl group, of 1 to 20 carbon atoms, such as methyl, ethyl, butyl, cyclohexyl and the like; or $R^{10}$ is an aromatic group, of 1 to 20 carbon atoms, such as phenyl, tolyl, naphthyl, and the like; or $R^{10}$ is an aralkyl group, of 1 to 20 carbon atoms, such as benzyl, cumyl, and the like;

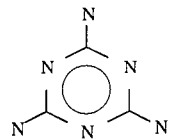
(3)

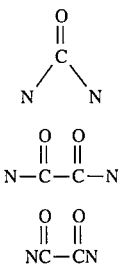
(4)
(5)
(6)

wherein R is an alkylene or an arylene group of 1 to 20 carbon atoms;

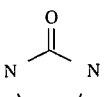
(7)

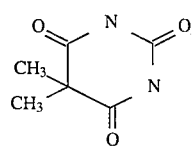
(8)

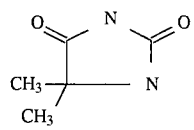
(9)

(10) polyfunctional carbamates;
(11) polyfunctional amides;
(12) hydantoins;
(13) dialkoxyethylene ureas;
(14) dihydroxyethylene urea represented by the formula:

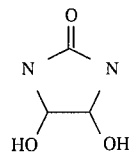

(15) homopolymers and copolymers containing carbamate units of the formula:

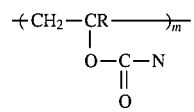

wherein R is hydrogen or alkyl, and m is at least 1;
(16) oligomeric derivatives thereof; and
(17) mixtures of any of (1) through (16).

The aminoplast may have, as a substituent, a hydrogen, an alkyl or an aryl group of 1 to about 20 carbon atoms, or a stabilizer reactive group such as —$CH_2OH$ and —$CH_2OR^9$ wherein $R^9$ is an alkyl group of 1 to about 20 carbon atoms or an aminoplast group-containing oligomeric group provided that the total number of stabilizer reactive groups per each aminoplast anchor is at least 1, and preferably more than 1.

The preferred aminoplast anchors of this invention are substantially fully etherified, substantially fully methylolated, substantially monomeric aminoplast crosslinkers commonly used in the coatings industry. They are characterized by having at least two, and preferably more than two, stabilizer-reactive groups per anchor molecule.

The most preferred aminoplast anchors of the invention are selected from a group consisting of substantially fully etherified, substantially fully methylolated, substantially monomeric glycoluril, melamine, benzoguanamine, cyclohexanecarboguanamine, urea, and mixtures thereof.

In addition to the substantially fully etherified, substantially monomeric amine-aldehyde aminoplast anchors described above, the non-etherified or partially etherified, substantially fully methylolated or partially methylolated monomeric and oligomeric aminoplasts are also usable in the composition of this invention.

Aminoplast anchors which contain very few alkoxymethyl groups generally have low solubilities due to the high N-H levels, and therefore are less preferred.

The most preferred aminoplast anchors are exemplified in greater detail below.

GLYCOLURIL ANCHORS

The most preferred glycoluril anchors of this invention are N-substituted glycolurils represented by the formula:

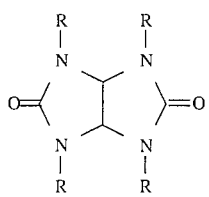

wherein at least two of the R groups are selected from the group consisting of methoxymethyl, ethoxymethyl, propoxymethyl, butoxymethyl, pentoxymethyl, hexoxymethyl, heptoxymethyl, octoxymethyl, nonoxymethyl, decoxymethyl and mixtures thereof, and the remaining R groups are selected from hydrogen, alkyl, hydroxymethyl, and glycoluril group-containing oligomeric moieties.

While it is preferable to have a multiplicity of alkoxymethyl groups per each glycoluril anchor molecule, under ordinary circumstances it is not necessary to obtain, for example, a pure tetra-substituted monomeric aminoplast such as N,N',N'',N'''-tetraalkoxymethylglycoluril represented by formula:

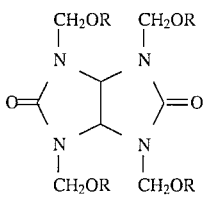

wherein R is an alkyl group of 1 to about 20 carbon atoms. The glycoluril may contain monomeric as well as oligomeric components.

The monomeric tetraalkoxyglycolurils themselves are not considered to be resinous materials since they are, as individual entities, non-polymeric compounds. They are considered, however, to be potential resin-forming compounds when subjected to heat, and particularly when subjected to heat under acidic conditions. As a result of the described resin-forming ability, the substantially monomeric glycoluril aminoplasts of this invention may produce, during the course of the reaction, varying amounts of oligomeric components such as dimers, trimers, and tetramers. The presence of varying amounts of these oligomeric forms is permissible and, indeed beneficial, particularly in cases where higher molecular weight and lower volatility products are desired as in the case of most applications in which the products are used as stabilizers against the degrading action of UV light. An example of glycoluril anchors of this invention is POWDERLINK® 1174 powder aminoplast resin, a product of American Cyanamid Company, Wayne, N.J. It has the following formula and properties:

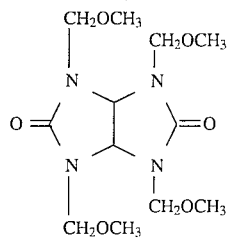

| | |
|---|---|
| Non Volatiles, minimum (% by weight) | 98 |
| Appearance | White to pale yellow granulated flakes |
| Melting Point (°C.) | 90–110° C. |
| Average Molecular Weight | 350 |
| Equivalent Weight | 90–125 |

Another example of a glycoluril anchor usable in this invention is CYMEL® 1170 fully butylated glycoluril resin, a product of American Cyanamid Company, Wayne, N.J., having the following properties:

| | |
|---|---|
| Non Volatiles, minimum (% by weight) | 95 |
| Appearance | Clear liquid |
| Color, Maximum (Gardner 1963) | 3 |
| Viscosity (Gardner-Holt, 25° C.) | X—$Z_2$ |
| Average Molecular Weight | 550 |
| Equivalent Weight | 150–230 |
| Methylol Content | Very low |

UREA ANCHORS

An example of a urea usable in this invention is BEETLE® 80 butylated urea-formaldehyde resin, a product of American Cyanamid Company, Wayne, N.J., having the following properties:

| | |
|---|---|
| Appearance | Clear Liquid |
| Color, Maximum (Gardner 1963) | 1 |
| Non-Volatiles (Weight %)* | 96 ± 2 |
| Viscosity (Gardner-Holt, 25° C.) | X—$Z_3$ |
| Solvent Tolerance (ASTM D1198-55) | >500 |

*Foil Method (45° C./45 min.)

MELAMINE ANCHORS

The melamine-based aminoplast anchors of this invention are well known per se, and have been used extensively as effective crosslinkers in coatings.

Unlike the tetrafunctional glycolurils, alkoxymethylmelamine functionality can be a maximum of six in a stabilizingly effective range of 1 to 6 stabilizer reactive alkoxymethyl groups per each melamine molecule.

Like the glycolurils, in addition to monomers, alkoxymethyl melamines can contain dimers, trimers, tetramers, and higher oligomers, each given combination of monomers and oligomers being preferred for a given application. For example, the lower viscosity monomerrich compositions are preferred for solvent-based high solids coatings.

An example of a substantially fully etherified, substantially fully methylolated, substantially monomeric melamines usable in this invention is CYMEL® 303 melamine crosslinking agent, a product of American Cyanamid Company, Wayne, N.J., which has the following formula and properties:

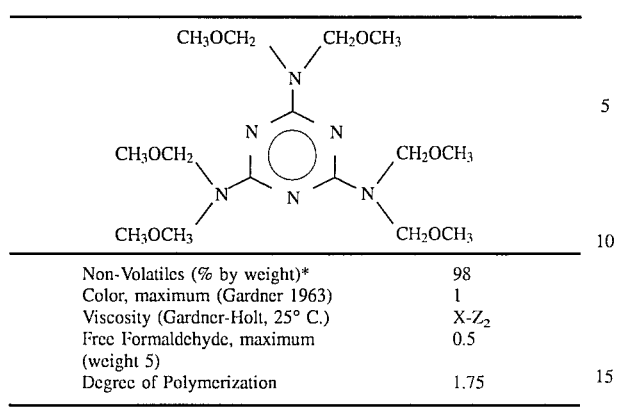

| | |
|---|---|
| Non-Volatiles (% by weight)* | 98 |
| Color, maximum (Gardner 1963) | 1 |
| Viscosity (Gardner-Holt, 25° C.) | X-Z₂ |
| Free Formaldehyde, maximum (weight %) | 0.5 |
| Degree of Polymerization | 1.75 |

*Foil Method (45° C./45 min.)

Another example of a substantially fully etherified, substantially fully methylolated, substantially monomeric melamine is CYMEL® 1168 aminoplast resin, a product of American Cyanamid Company, Wayne, N.J. The alkyl group in CYMEL® 1168 consists essentially of a mixture of methyl and isobutyl groups.

It has the following formula (wherein R=methyl or isobutyl) and properties:

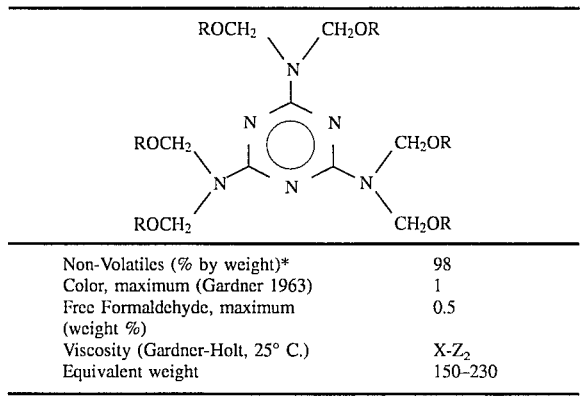

| | |
|---|---|
| Non-Volatiles (% by weight)* | 98 |
| Color, maximum (Gardner 1963) | 1 |
| Free Formaldehyde, maximum (weight %) | 0.5 |
| Viscosity (Gardner-Holt, 25° C.) | X-Z₂ |
| Equivalent weight | 150–230 |

*Foil Method (45° C./45 min.)

An example of substantially methylolated, partially etherified, substantially oligomeric melamine is CYMEL® 370 crosslinking agent, a product of American Cyanamid Company, Wayne, N.J. It has the following properties:

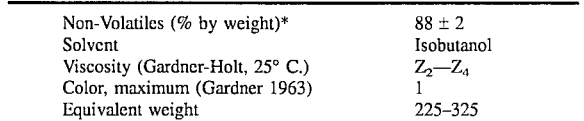

| | |
|---|---|
| Non-Volatiles (% by weight)* | 88 ± 2 |
| Solvent | Isobutanol |
| Viscosity (Gardner-Holt, 25° C.) | Z₂–Z₄ |
| Color, maximum (Gardner 1963) | 1 |
| Equivalent weight | 225–325 |

*Foil Method (45° C./45 min.)

GUANAMINE ANCHORS

As in melamines, the partially or fully methylolated or etherified alkyl and aryl guanamine aminoplasts, both in their monomeric and oligomeric forms, are usable as anchors in this invention, with the selection depending on the particular application or the properties desired in the product.

Benzoguanamine, cyclohexylcarboguanamine and acetoguanamine aminoplasts are especially preferred as anchors in this invention. The benzoguanamines are represented by the formula:

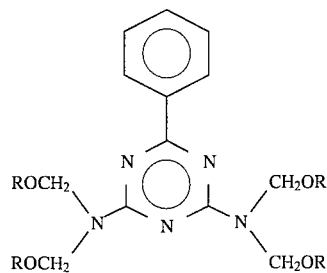

wherein R is an alkyl group of 1 to about 20 carbon atoms, or a mixture thereof. An example of a benzoguanamine-based anchor is CYMEL® 1123 resin as described above, wherein R is a mixture of methyl and ethyl groups.

The acetoguanamine-based anchors are represented by the formula:

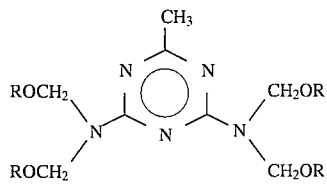

wherein R is an alkyl group of 1 to about 20 carbon atoms, or a mixture thereof.

The cyclohexylcarboguanamine-based anchors are represented by the formula:

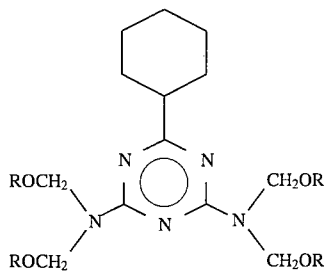

wherein R is an alkyl group of 1 to about 20 carbon atoms, or a mixture thereof.

It is evident from the above, that a person skilled in the art, in selecting suitable anchors for a particular application, may choose a mixture thereof which imparts a balance of properties desired for that particular application.

PENDENT PHENOLIC STABILIZERS

The phenolic stabilizers useful as reactants may be in the free phenolic form (R=H, infra) or it may be in the blocked form (R=a group other than hydrogen, such as a acetyl group, or a trimethylsilyl group, or an ethyl group, infra).

The blocked and unblocked phenols usable in the preparation of the novel aminoplast anchored stabilizers of the invention are represented by the formula:

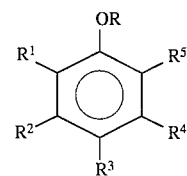

wherein $R^1$ is selected from the group consisting of:

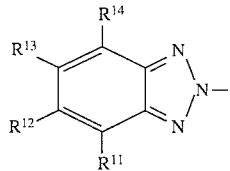

(j)

wherein each of $R^{11}$ through $R^{14}$ is independently selected from the group consisting of alkyl of 1 to 20 carbon atoms, alkoxy of 1 to 20 carbon atoms, aralkyl of 7 to 20 carbon atoms, hydrogen, chloro, bromo, cyano, and nitro group;

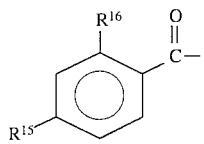

(k)

wherein each of $R^{15}$ and $R^{16}$ is independently selected from the group consisting of alkyl of 1 to 20 carbon atoms, aralkyl of 7 to 20 carbon atoms, alkoxy of 1 to 20 carbon atoms, hydrogen, chloro, bromo, cyano, nitro, and hydroxy groups;

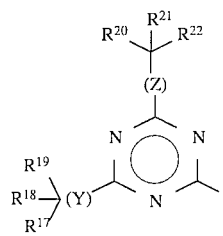

(l)

wherein Y and Z are the same or different aromatic carbocyclic radicals; and wherein each of $R^{17}$ through $R^{22}$ is independently selected from the group consisting of alkyl of 1 to 20 carbon atoms, alkoxy of 1 to 20 carbon atoms, hydrogen, chloro, bromo, cyano, carboxy, and nitro groups;

(m) carboxylic acid group or amides and esters thereof;

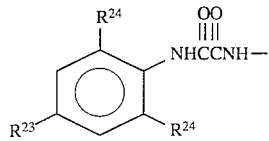

(n)

wherein each of $R^{23}$ and $R^{24}$ is the same or different, and is independently selected from the group consisting of alkyl of 1 to 20 carbon atoms, aralkyl of 7 to 20 carbon atoms, alkoxy of 1 to 20 carbon atoms, hydrogen, chloro, bromo, cyano, and nitro groups; and (o) mixtures thereof; and wherein $R^2$ is selected from the group consisting of hydrogen, alkyl of 1 to 20 carbon atoms, and aralkyl of 7 to 20 carbon atoms; and wherein $R^3$ is selected from the group consisting of hydrogen, alkyl of 1 to 20 carbon atoms, aralkyl of 7 to 20 carbon atoms, and alkyl of 1 to 20 carbon atoms which is interrupted, substituted, or interrupted and substituted by one or more oxygen, carbonyl, or carboxy groups; and wherein $R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl of 1 to 20 carbon atoms which is interrupted, substituted, or interrupted and substituted by one or more oxygen, carbonyl, or carboxy groups;

wherein $R^5$ is selected from the group consisting of hydrogen, alkyl of 1 to 20 carbon atoms, and aralkyl of 7 to 20 carbon atoms; and wherein R is selected from the group consisting of hydrogen, alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

The unblocked stabilizers are generally more active than their corresponding blocked counterparts as ultraviolet light stabilizers because of the well recognized interaction of the hydrogen atom on the hydroxy group of the stabilizer with a neighboring group such as a carbonyl, an ester, or an $sp^2$ hybridized nitrogen atom.

The blocked stabilizers, however, are capable of deblocking either under processing conditions or under use conditions thereby producing the generally more active unblocked forms.

Deblocking may be effected by the action of acids, bases, heat, moisture, or oxidative processes initiated by free radicals or atmospheric oxygen.

The phenolic stabilizers usable in this invention are well known in the art and include a variety of UV absorbers.

Various classes of phenolic UV stabilizers suitable for use in the preparation of the aminoplast anchored novel stabilizers of the invention are exemplified in greater detail below:

A. BENZOTRIAZOLES

The benzotriazole type UV stabilizers usable in the preparation of the stabilizers of the invention are a widely known class of UV absorbers, and are represented by the formula:

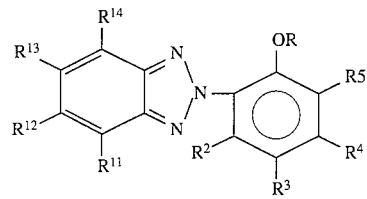

wherein each of $R^{11}$ through $R^{14}$ is independently selected from the group consisting of alkyl of 1 to 20 carbon atoms, alkoxy of 1 to 20 carbon atoms, aralkyl of 7 to 20 carbon atoms, hydrogen, chloro, bromo, cyano, and nitro groups;

wherein $R^2$ is selected from the group consisting of hydrogen, alkyl of 1 to 20 carbon atoms, and aralkyl of 7 to 20 carbon atoms;

wherein $R^3$ is selected from the group consisting of hydrogen, alkyl of 1 to 20 carbon atoms, aralkyl of 7 to 20 carbon atoms, and alkyl of 1 to 20 carbon atoms which is interrupted, substituted, or interrupted and substituted by one or more oxygen, carbonyl, or carboxy groups;

wherein $R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl of 1 to 20 carbon atoms which is interrupted, substituted, or interrupted and substituted by one or more oxygen, carbonyl, or carboxy groups;

wherein
$R^5$ is selected from the group consisting of hydrogen, alkyl of 1 to 20 carbon atoms, and aralkyl of 7 to 20 carbon atoms; and wherein
R is selected from the group consisting of hydrogen, alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

The preferred benzotriazole type stabilizers usable as starting material in the preparation of the aminoplast-anchored stabilizers of the invention are represented by the formulae:

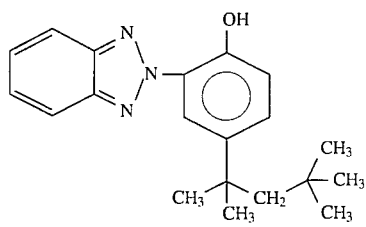

Cyasorb ® UV 5411 Light Stabilizer (a product of American Cyanamid Company, Wayne, New Jersey) and

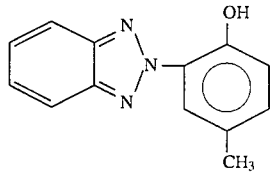

B. BENZOPHENONES

The benzophenone type UV stabilizers usable in the preparation of the stabilizers of the invention are represented by the formula:

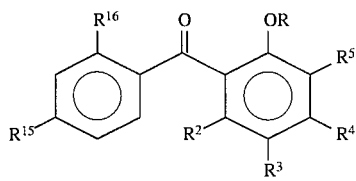

wherein each of $R^{15}$ and $R^{16}$ is independently selected from the group consisting of alkyl of 1 to 20 carbon atoms, alkoxy of 1 to 20 carbon atoms, hydrogen, chloro, bromo, cyano, nitro, and hydroxy groups;

wherein
$R^2$ is selected from the group consisting of hydrogen, alkyl of 1 to 20 carbon atoms, and aralkyl of 7 to 20 carbon atoms;

wherein
$R^3$ is selected from the group consisting of hydrogen, alkyl of 1 to 20 carbon atoms, aralkyl of 7 to 20 carbon atoms, and alkyl which is interrupted, substituted or interrupted and substituted by one or more oxygen, carbonyl, or carboxy groups;

wherein
$R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl which is interrupted, substituted, or interrupted and substituted by one or more oxygen, carbonyl, or carboxy groups;

wherein
$R^5$ is selected from the group consisting of hydrogen, alkyl of 1 to 20 carbon atoms, and aralkyl of 7 to 20 carbon atoms; and wherein
R is selected from the group consisting of hydrogen, alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

The preferred benzophenone type stabilizers are represented by the formulae, all products of the American Cyanamid Company, Wayne, N.J.:

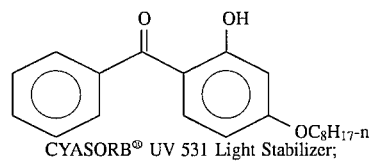

CYASORB® UV 531 Light Stabilizer;

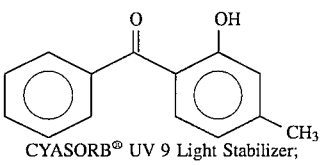

CYASORB® UV 9 Light Stabilizer;

and

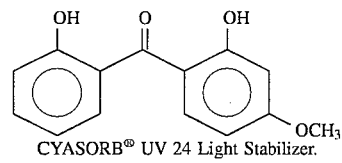

CYASORB® UV 24 Light Stabilizer.

C. ARYLTRIAZINES

The aryltriazine type UV absorbers usable as starting materials are represented by the formula:

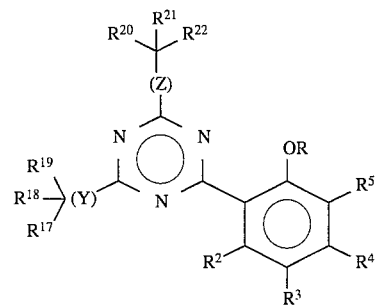

wherein
Y and Z are the same or different aromatic carbocyclic radicals;

wherein
each of $R^{17}$ through $R^{22}$ is the same or different and is independently selected from the group consisting of alkyl of 1 to 20 carbon atoms, alkoxy of 1 to 20 carbon atoms, hydrogen, chloro, bromo, cyano, carboxy, and nitro groups;

wherein
R² is selected from the group consisting of hydrogen, alkyl of 1 to 20 carbon atoms, and aralkyl of 7 to 20 carbon atoms;
wherein
R³ is selected from the group consisting of hydrogen, alkyl of 1 to 20 carbon atoms, aralkyl of 7 to 20 carbon atoms, and alkyl which is interrupted, substituted, or interrupted and substituted by one or more oxygen, carbonyl, or carboxy groups;
wherein
R⁴ is selected from the group consisting of hydrogen, hydroxy, alkyl of 1 to 20 carbon atoms, aralkyl of 7 to 20 carbon atoms, alkoxy of 1 to 20 carbon atoms, and alkyl which is interrupted, substituted, or interrupted and substituted by one or more oxygen, carbonyl, or carboxy groups;
wherein
R⁵ is selected from the group consisting of hydrogen, alkyl of 1 to 20 carbon atoms, and aralkyl of 7 to 20 carbon atoms; and
wherein
R is selected from the group consisting of hydrogen, alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

The preferred aryltriazine UV stabilizers usable as starting materials in the preparation of the anchored stabilizers of the invention are represented by the formula:

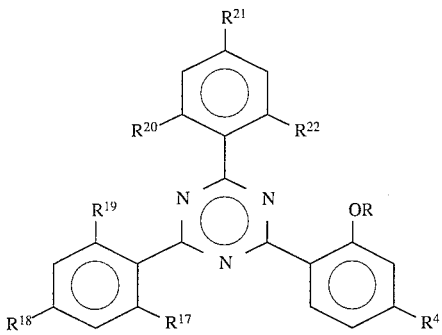

wherein each of R¹⁷ through R²² is independently selected from the group consisting of alkyl of 1 to 20 carbon atoms, alkoxy of 1 to 20 carbon atoms, hydrogen, chloro, bromo, cyano, and nitro groups; and
wherein R and R⁴ have the same meaning as above.

An example of the preferred aryltriazine type UV stabilizer is represented by the formula:

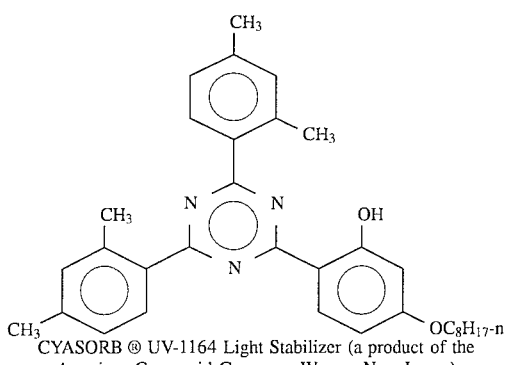

CYASORB ® UV-1164 Light Stabilizer (a product of the American Cyanamid Company, Wayne, New Jersey)

D. SALICYLIC ACID DERIVATIVES

The salicylic acid type stabilizers suitable for use as starting materials are represented by the formula:

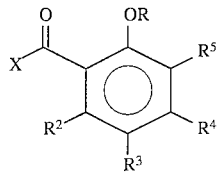

wherein
X is selected from the group consisting of morpholino, piperidino, pyrrolidino groups, OR³⁰, and NR³¹R³² groups;
wherein R³⁰ is selected from the group consisting of hydrogen, silyl, alkyl of 1 to 20 carbon atoms, aryl of 1 to 20 carbon atoms, aralkyl of 7 to 20 carbon atoms, and mixtures thereof; and
wherein each of R³¹ and R³² is the same or different and is selected from the group consisting of hydrogen, alkyl of 1 to 20 carbon atoms, aryl of 6 to 20 carbon atoms, and aralkyl of 7 to 20 carbon atoms;
wherein
R², R³, R⁴, and R⁵ are the same or different and each is selected from the group consisting of hydrogen, alkyl of 1 to 20 carbon atoms, and aralkyl of 7 to 20 carbon atoms; and
wherein
R is selected from the group consisting of hydrogen, alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

The preferred class of salicylic acid or its esters is represented by the formula:

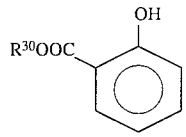

wherein R³⁰ is selected from the group consisting of hydrogen, alkyl of 1 to 20 carbon atoms, aryl of 1 to 20 carbon atoms, aralkyl of 7 to 20 carbon atoms, and mixtures thereof.

E. OXANILIDES

The oxanilide type stabilizers suitable for use as starting materials in the preparation of the aminoplast anchored stabilizers of the invention are represented by the formula:

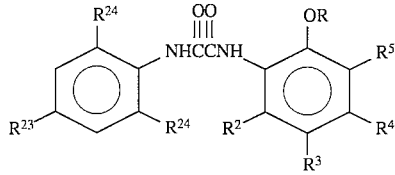

wherein each of R²³ and R²⁴ is the same or different, and is independently selected from the group consisting of alkyl of 1 to 20 carbon atoms, aralkyl of 7 to 20 carbon atoms, alkoxy of 1 to 20 carbon atoms, hydrogen, chloro, bromo, cyano, and nitro groups;
wherein
R² is selected from the group consisting of hydrogen, alkyl of 1 to 20 carbon atoms, and aralkyl of 7 to 20 carbon atoms;

wherein
R³ is selected from the group consisting of hydrogen, alkyl of 1 to 20 carbon atoms, aralkyl of 7 to 20 carbon atoms, and alkyl which is interrupted, substituted, or interrupted and substituted by one or more oxygen, carbonyl, or carboxy groups;

wherein
R⁴ is selected from the group consisting of hydrogen, hydroxy, alkyl of 1 to 20 carbon atoms, alkoxy of 1 to 20 carbon atoms, aralkyl of 7 to 20 carbon atoms, and alkyl which is interrupted, substituted, or interrupted and substituted by one or more oxygen, carbonyl, and carboxy groups;

wherein
R⁵ is selected from the group consisting of hydrogen, alkyl of 1 to 20 carbon atoms; and aralkyl of 7 to 20 carbon atoms; and wherein
R is selected from the group consisting of hydrogen, alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

The preferred oxanilide is SANDOVUR® 3206 light stabilizer, a product of Sandoz Corporation, Basel, Switzerland, represented by the formula:

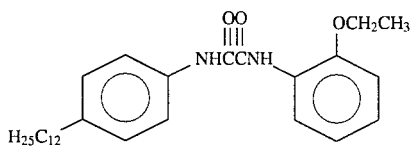

ANCHORED PRODUCTS
AMINOPLAST ANCHORED UNBLOCKED STABILIZERS

The unblocked aminoplast anchored phenolic UV stabilizers of the invention are represented by the formula:

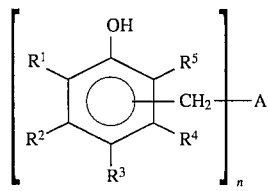

wherein
A is a an m functional aminoplast anchor molecule to which n phenol rings are attached through n methylene bridges, said bridges replacing R³, R⁴, or R⁵ groups on said phenol rings, which aminoplast anchor molecule is selected from the group consisting of:

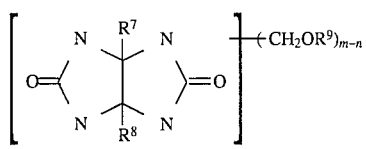

wherein R⁷ and R⁸ are independently selected from the group consisting of hydrogen, alkyl of 1 to 20 carbon atoms, aryl of 6 to 20 carbon atoms, and aralkyl of 7 to 20 carbon atoms; and wherein R⁹ is a linear or branched alkyl group of 1 to carbon atoms;

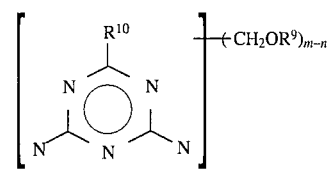

wherein R¹⁰ is selected from the group consisting of alkyl of 1 to 20 carbon atoms, aryl of 6 to 20 carbon atoms, and aralkyl of 7 to 20 carbon atoms; and wherein R⁹ is a linear or branched alkyl group of 1 to 20 carbon atoms;

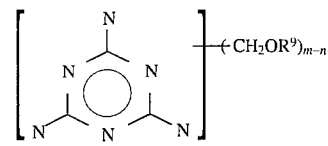

wherein R⁹ is a linear or branched alkyl group of 1 to 20 carbon atoms;

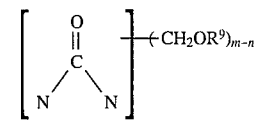

wherein R⁹ is a linear or branched alkyl group of 1 to 20 carbon atoms;

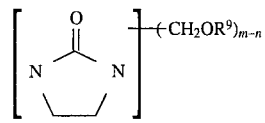

wherein R⁹ is a linear or branched alkyl group of 1 to 20 carbon atoms;

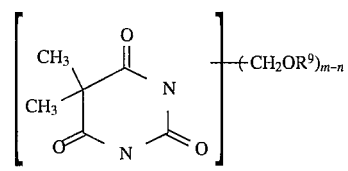

wherein R⁹ is a linear or branched alkyl group of 1 to 20 carbon atoms;

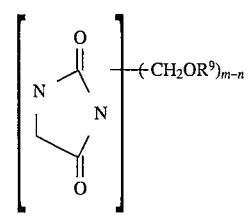

wherein R⁹ is a linear or branched alkyl group of 1 to 20 carbon atoms (h) oligomeric aminoplast anchor molecules derived from the self- or cross-condensation of any of (a) through (g) or mixtures thereof;

(i) mixtures of any of (a) through (h) ;

wherein m is at least 1; and wherein n is more than 0.5; and wherein R¹ is selected from the group consisting of:

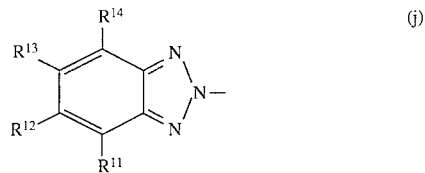

wherein each of R¹¹ through R¹⁴ is independently selected from the group consisting of alkyl of 1 to 20 carbon atoms, alkoxy or 1 to 20 carbon atoms, aralkyl of 7 to 20 carbon atoms, hydrogen, chloro, bromo, cyano, and nitro groups;

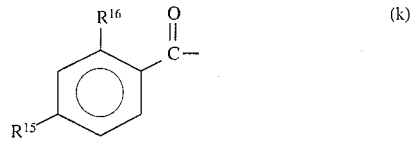

wherein each of R¹⁵ and R¹⁶ is independently selected from the group consisting of alkyl of 1 to 20 carbon atoms, aralkyl of 7 to 20 carbon atoms, alkoxy of 1 to 20 carbon atoms, hydrogen, chloro, bromo, cyano, nitro and hydroxy groups;

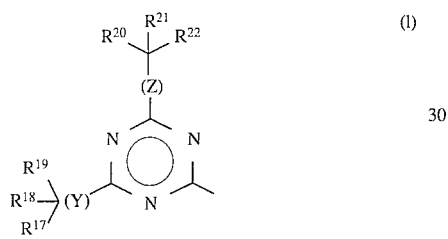

wherein each of R¹⁷ through R²² is independently selected from the group consisting of alkyl of 1 to 20 carbon atoms, alkoxy of 1 to 20 carbon atoms, hydrogen, chloro, bromo, cyano, and nitro groups;
(m) carboxylic group or amides and esters thereof;

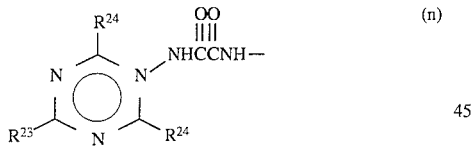

wherein each of R²³ and R²⁴ is independently selected from the group consisting of alkyl of 1 to 20 carbon atoms, aralkyl of 7 to 20 carbon atoms, alkoxy of 1 to 20 carbon atoms, hydrogen, chloro, bromo, cyano, and nitro groups; and
(o) mixtures thereof; and
wherein
R² is selected from the group consisting of hydrogen, alkyl of 1 to 20 carbon atoms, and aralkyl of 7 to 20 carbon atoms;
wherein
R³ is selected from the group consisting of hydrogen, alkyl of 1 to 20 carbon atoms, aralkyl of 7 to 20 carbon atoms, and alkyl of 1 to 20 carbon atoms which is interrupted, substituted, or interrupted and substituted by one or more oxygen, carbonyl, or carboxy groups;
wherein
R⁴ is selected from the group consisting of hydrogen, hydroxy, alkyl of 1 to 20 carbon atoms, aralkyl of 7 to 20 carbon atoms, and alkyl of 1 to 20 carbon atoms which is interrupted, substituted, or interrupted and substituted by one or more oxygen, carbonyl, and carboxy groups; and
wherein
R⁵ is selected from the group consisting of hydrogen, alkyl of 1 to 20 carbon atoms, and aralkyl of 7 to 20 carbon atoms.

The stabilizer to aminoplast ratio in the anchored stabilizers of the invention is greater than 0.5:1, preferably the ratio is greater than 1:1, and most preferably the ratio is greater than 2:1.

AMINOPLAST ANCHORED BENZOTRIAZOLE STABILIZERS

The unblocked benzotriazole type aminoplast anchored stabilizers are represented by the formula:

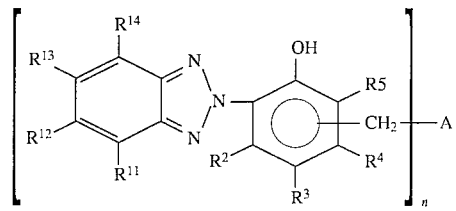

wherein
A is an m functional aminoplast anchor molecule to which n phenol rings are attached through n methylene bridges, said bridges replacing R³, R⁴, or R⁵ groups on said phenol rings, which aminoplast anchor molecule is selected from the group consisting of:

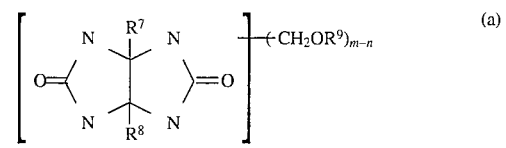

wherein R⁷ and R⁸ are independently selected from the group consisting of hydrogen, alkyl of 1 to 20 carbon atoms, aryl of 6 to 20 carbon atoms, and aralkyl of 7 to 20 carbon atoms; and wherein R⁹ is a linear or branched alkyl group of 1 to 20 carbon atoms;

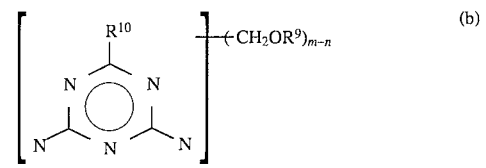

wherein R¹⁰ is selected from the group consisting of alkyl of 1 to 20 carbon atoms, aryl of 6 to 20 carbon atoms, and aralkyl of 7 to 20 carbon atoms; and wherein R⁹ is a linear or branched alkyl group of 1 to 20 carbon atoms;

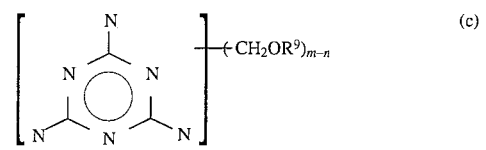

wherein R⁹ is a linear or branched alkyl group of 1 to 20 carbon atoms;

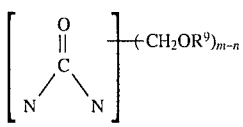  (d)

wherein $R^9$ is a linear or branched alkyl group of 1 to 20 carbon atoms;

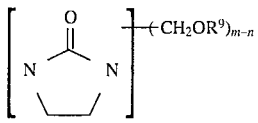  (e)

wherein $R^9$ is a linear or branched alkyl group of 1 to 20 carbon atoms;

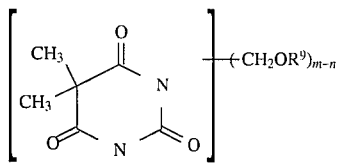  (f)

wherein $R^9$ is a linear or branched alkyl group of 1 to 20 carbon atoms;

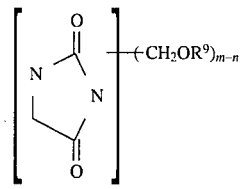  (g)

wherein $R^9$ is a linear or branched alkyl group of 1 to 20 carbon atoms;

(h) oligomeric aminoplast anchor molecules derived from self- or cross-condensation of any of (a) through (g) and mixtures thereof; and (i) mixtures of any of (a) through (h) ;

wherein m is at least 1; and wherein n is more than 0.5; and wherein
each of $R^{11}$ through $R^{14}$ is independently selected from the group consisting of alkyl of 1 to 20 carbon atoms, alkoxy of 1 to 20 carbon atoms, aralkyl of 7 to 20 carbon atoms, hydrogen, chloro, bromo, cyano, and nitro groups;

wherein
$R^2$ is selected from the group consisting of hydrogen, alkyl of 1 to 20 carbon atoms, and aralkyl of 7 to 20 carbon atoms;

wherein
$R^3$ is selected from the group consisting of hydrogen, alkyl of 1 to 20 carbon atoms, aralkyl of 7 to 20 carbon atoms, and alkyl which is interrupted, substituted, or interrupted and substituted by one or more oxygen, carbonyl, or carboxy groups;

wherein
$R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl which is interrupted, substituted, or interrupted and substituted by one or more oxygen, carbonyl, and carboxy groups; and wherein
$R^5$ is selected from the group consisting of hydrogen, alkyl of 1 to 20 carbon atoms, and aralkyl of 7 to 20 carbon atoms.

More specifically, the benzotriazole type aminoplast anchored stabilizers may be represented by the formula:

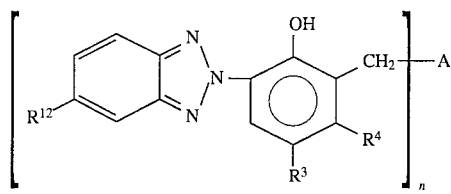

wherein
A is an m functional aminoplast anchor molecule to which n phenol rings are attached through n methylene bridges at a point of attachment ortho- to the point of attachment of the hydroxy group, which aminoplast anchor molecule is selected from the group consisting of:

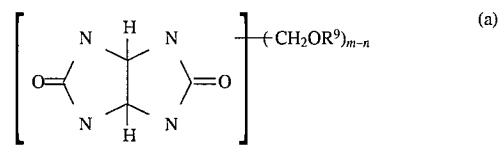  (a)

wherein $R^9$ is selected from the group consisting of methyl, ethyl, 1-propyl, 2-propyl, 1-butyl, 2-butyl, and mixtures thereof;

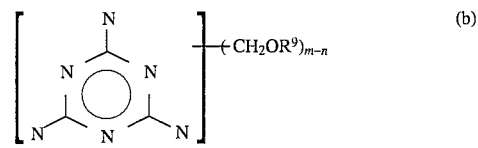  (b)

wherein $R^9$ is selected from the group consisting of methyl, ethyl, 1-propyl, 2-propyl, 1-butyl, 2-butyl, and mixtures thereof;

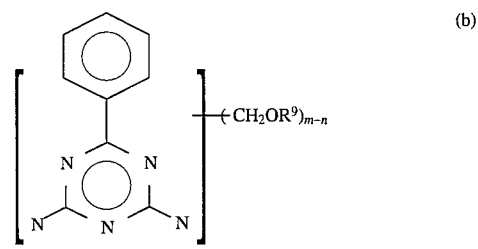  (b)

wherein $R^9$ is selected from the group consisting of methyl, ethyl, 1-propyl, 2-propyl, 1-butyl, 2-butyl, and mixtures thereof;

(d) oligomeric aminoplast anchor molecules derived from self- or cross-condensation of (a), (b), (c), or mixtures thereof; and (e) mixtures of any of (a) through (d);

wherein m is at least 1; and wherein n is more than 0.5; and wherein
$R^{12}$ is selected from the group consisting of methyl, ethyl, methoxy, ethoxy, hydrogen, and chloro groups;

wherein
$R^3$ is selected from the group consisting of hydrogen, methyl, ethyl, tertiary butyl, tertiary pentyl, tertiary octyl, hydroxyethyl, and betapropionic acid esters; and wherein R$^4$ is selected from the group consisting of hydrogen, hydroxy, hydroxyethoxy, and hydroxyhexoxy groups.

Glycoluril type aminoplasts, wherein R$^9$ in the alkoxymethylglycoluril is a mixture of methyl and ethyl groups, may also be used, particularly when higher solubility of the product in organic solvents is desired.

The preferred benzotriazole type aminoplast anchored stabilizers are those represented by the formula:

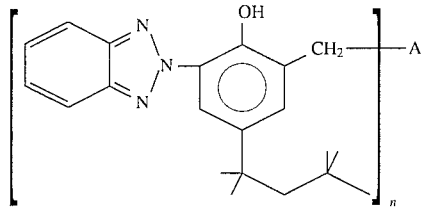

wherein

A is an m functional aminoplast anchor molecule to which n phenol rings are attached through n methylene bridges at a point of attachment ortho- to the point of attachment of the hydroxy group, which aminoplast anchor molecule is selected from the group consisting of:

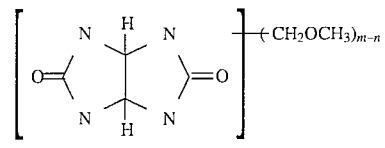

(a)

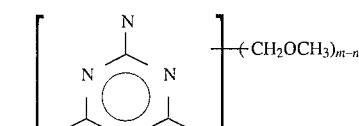

(b)

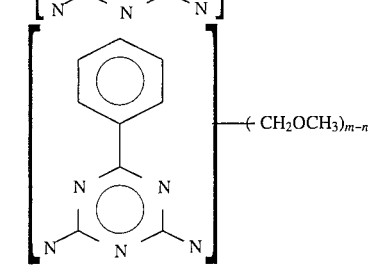

(c)

(d) oligomeric aminoplast anchor molecules derived from self- or cross-condensation of (a), (b), (c) or mixtures or thereof; and (e) mixtures of any of (a) through (d);

wherein m is at least 1; and wherein n is more than 0.5.

Examples of the preferred embodiments are:

A. 5-Octyl substituted benzotriazoles represented by the formula:

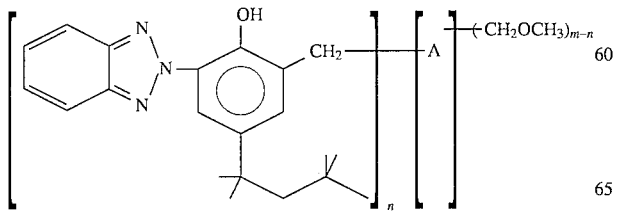

wherein A is a glycoluril anchor; wherein m is 2 to 14 and n is in the range of from 1 to 14; wherein the ratio of hydroxyarylbenzotriazole to glycoluril is from about 1:1 to about 4:1; and wherein the glycoluril is a mixture of monomeric, dimeric, trimeric, tetrameric, and higher oligomeric units.

B. 5-Methyl substituted benzotriazoles represented by the formula:

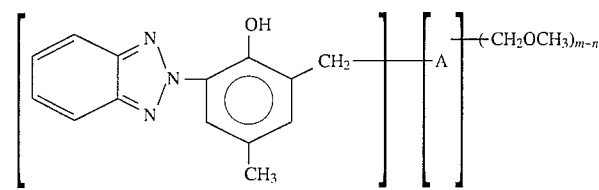

wherein A is a glycoluril anchor; wherein m is 2 to 14 and n is in the range of from about 1 to 14; wherein the ratio of hydroxyarylbenzotriazole to glycoluril is from about 1:1 to about 4:1; and wherein the glycoluril is a mixture of monomeric dimeric, trimeric, tetrameric, and higher oligomeric units.

AMINOPLAST ANCHORED BENZOPHENONE STABILIZERS

The unblocked benzophenone type aminoplast anchored stabilizers are represented by the formula:

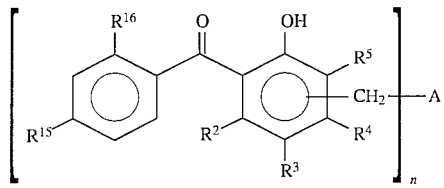

wherein

A is an m functional aminoplast anchor molecule to which n phenol rings are attached through n methylene bridges, said bridges replacing R$^3$, R$^4$, or R$^5$ groups on said phenol rings, which aminoplast anchor molecule is selected from the group consisting of:

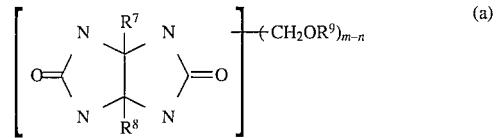

(a)

wherein R$^7$ and R$^8$ are independently selected from the group consisting of hydrogen, alkyl of 1 to 20 carbon atoms, aryl of 6 to 20 carbon atoms, and aralkyl of 7 to 20 carbon atoms, and wherein R$^9$ is a linear or branched alkyl group of 1 to 20 carbon atoms;

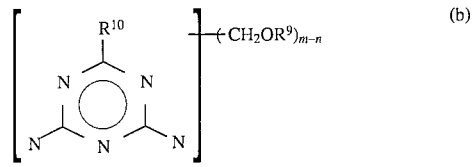

(b)

wherein R$^{10}$ is selected from the group consisting of alkyl of 1 to 20 carbon atoms, aryl of 6 to 20 carbon atoms, and aralkyl of 7 to 20 carbon atoms; and wherein R$^9$ is a linear or branched alkyl group of 1 to 20 carbon atoms;

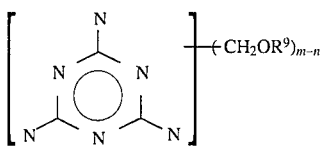  (c)

wherein $R^9$ is a linear or branched alkyl group of 1 to 20 carbon atoms;

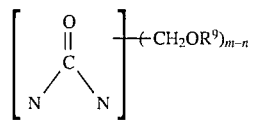  (d)

wherein $R^9$ is a linear or branched alkyl group of 1 to 20 carbon atoms;

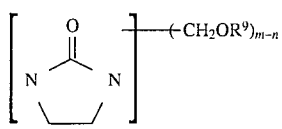  (e)

wherein $R^9$ is a linear or branched alkyl group of 1 to 20 carbon atoms;

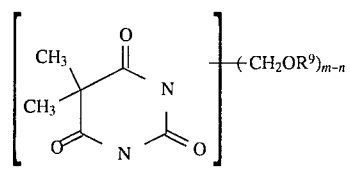  (f)

wherein $R^9$ is a linear or branched alkyl group of 1 to 20 carbon atoms;

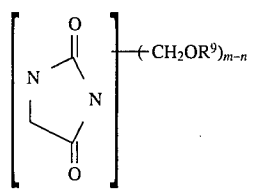  (g)

wherein $R^9$ is a linear or branched alkyl group of 1 to 20 carbon atoms;

(h) oligomeric aminoplast anchor molecules derived from self- or cross-condensation of any of (a) through (g) and mixtures thereof; and (i) mixtures of any of (a) through (h);

wherein m is at least 1; and wherein n is more than 0.5; and wherein
each of $R^{15}$ and $R^{16}$ is independently selected from the group consisting of alkyl of 1 to 20 carbon atoms, aralkyl of 7 to 20 carbon atoms, alkoxy of 1 to 20 carbon atoms, hydrogen, chloro, bromo, cyano, nitro, and hydroxy groups;

wherein
$R^2$ is selected from the group consisting of hydrogen, alkyl of 1 to 20 carbon atoms, and aralkyl of 7 to 20 carbon atoms;

wherein
$R^3$ is selected from the group consisting of hydrogen, alkyl of 1 to 20 carbon atoms, aralkyl of 7 to 20 carbon atoms, and alkyl which is interrupted, substituted or interrupted and substituted by one or more oxygen, carbonyl, or carboxy groups;

wherein
$R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl which is interrupted, substituted, or interrupted and substituted by one or more oxygen, carbonyl, or carboxy groups; and wherein
$R^5$ is selected from the group consisting of hydrogen, alkyl of 1 to 20 carbon atoms, and aralkyl of 7 to 20 carbon atoms.

More specifically, the benzophenone type aminoplast anchored stabilizers may be represented by the formula:

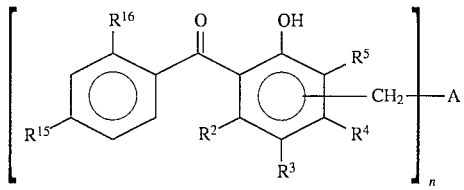

wherein
A is m functional aminoplast anchor molecule to which n phenol rings are attached through n methylene bridges at a point of attachment ortho- or para- to the point of attachment of the hydroxy group, which aminoplast anchor molecule is selected from the group consisting of:

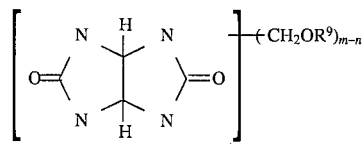  (a)

wherein $R^9$ is selected from the group consisting of methyl, ethyl, 1-propyl, 2-propyl, 1-butyl, 2-butyl, and mixtures thereof;

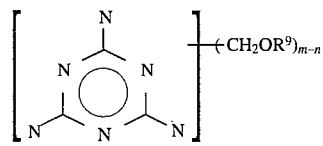  (b)

wherein $R^9$ is selected from the group consisting of methyl, ethyl, 1-propyl, 2-propyl, 1-butyl, 2-butyl, and mixtures thereof;

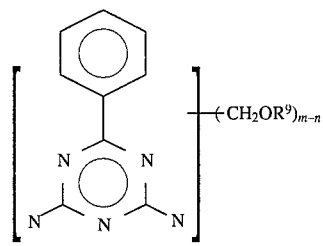  (c)

wherein $R^9$ is selected from the group consisting of methyl, ethyl, 1-propyl, 2-propyl, 1-butyl, 2-butyl, and mixtures thereof;

(d) oligomeric aminoplast anchor molecules derived from self- or cross-condensation of (a), (b), (c), or mixtures thereof; and (e) mixtures of any of (a) through (d);

wherein m is at least 1; and wherein n is more than 0.5; and wherein
each of $R^{15}$ and $R^{16}$ is independently selected from the group consisting of hydrogen, hydroxy, and alkoxy of 1 to 20 carbon atoms; and wherein
$R^4$ is selected from the group consisting of hydrogen, hydroxy, and alkoxy of 1 to 20 carbon atoms.

The preferred aminoplast anchor molecules are selected from the group consisting of:

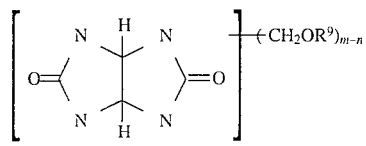 (a)

wherein $R^9$ is selected from the group consisting of methyl, ethyl, 1-propyl, 2-propyl, 1-butyl, 2-butyl, and mixtures thereof;

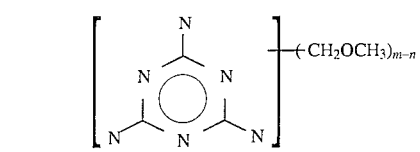 (a)

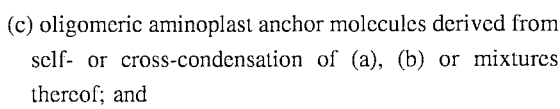 (b)

(c) oligomeric aminoplast anchor molecules derived from self- or cross-condensation of (a), (b) or mixtures thereof; and (d) mixtures of any of (a) through (c);

wherein m is at least 1; and wherein n is more than 0.5.

The most preferred benzophenone type aminoplast anchored stabilizers are represented by the formulae:

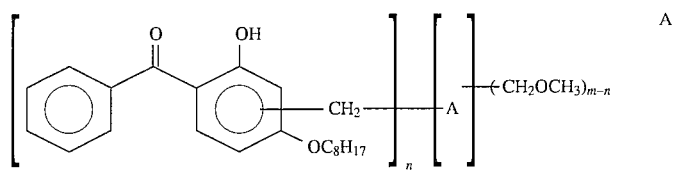 A wherein A is a glycoluril anchor; and
wherein the methylene bridge is at a point of attachment ortho- or para- to the point of attachment of the hydroxy group; and wherein m is 2 to 14 and n is in the range of from about 1 to 14, wherein the ratio of benzophenone to glycoluril is from about 1:1 to about 4:1, and wherein the glycoluril is a mixture of monomeric, dimeric, trimeric, tetrameric, and higher oligomeric units;

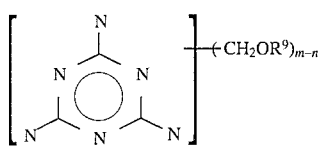 (b)

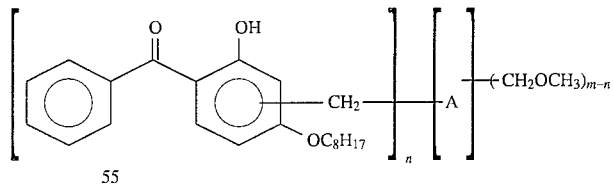 B wherein $R^9$ is selected from the group consisting of methyl, ethyl, 1-propyl, 2-propyl, 1-butyl, 2-butyl, and mixtures thereof;

(c) oligomeric aminoplast anchor molecules derived from self- or cross-condensation of (a), (b), or mixtures thereof; and (d) mixtures of any of (a) through (c); and more particularly, they are selected from the group consisting of:

wherein A is a melamine anchor; and
wherein the methylene bridge is at a point of attachment orth- or para- to the point of attachment of the hydroxy group and wherein m is from 3 to 16 and n is in the range of 1 to 16, wherein the ratio of benzophenones to melamines is from about 1:1 to about 6:1, and wherein the melamine is a mixture of monomeric, dimeric, trimeric, tetrameric, and higher oligomeric units.

AMINOPLAST ANCHORED ARYLTRIAZINE STABILIZERS

The unblocked aryltriazine type aminoplast anchored stabilizers are represented by the formula:

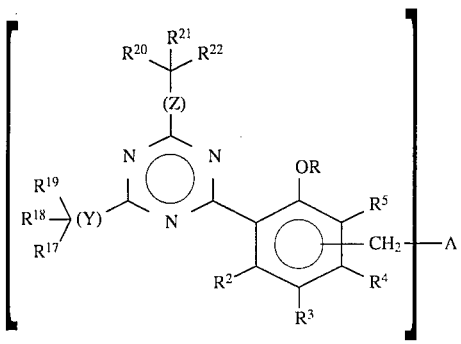

wherein
each of Y and Z is the same or different aromatic carbocyclic radicals;
wherein
each of $R^{17}$ through $R^{22}$ is the same or different and is independently selected from the group consisting of alkyl of 1 to 20 carbon atoms, alkoxy of 1 to 20 carbon atoms, hydrogen, chloro, bromo, cyano, carboxy, and nitro groups; and
wherein
A is an m functional aminoplast anchor molecule to which n phenol rings are attached through n methylene bridges, said bridges replacing $R^2$, $R^3$, $R^4$, or $R^5$ groups on said phenol rings, which aminoplast anchor molecule is selected from the group consisting of:

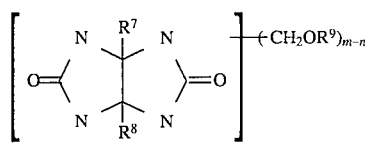
(a)

wherein $R^7$ and $R^8$ are independently selected from the group consisting of hydrogen, alkyl of 1 to 20 carbon atoms, aryl of 6 to 20 carbon atoms, and aralkyl of 7 to 20 carbon atoms; and wherein $R^9$ is a linear or branched alkyl group of 1 to 20 carbon atoms;

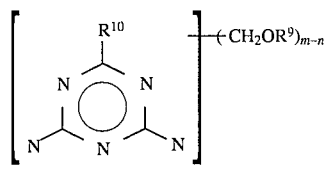
(b)

wherein $R^{10}$ is selected from the group consisting of alkyl of 1 to 20 carbon atoms, aryl of 6 to 20 carbon atoms, and aralkyl of 7 to 20 carbon atoms; and wherein $R^9$ is a linear or branched alkyl group of 1 to 20 carbon atoms;

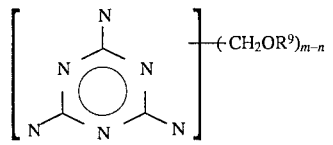
(c)

wherein $R^9$ is a linear or branched alkyl group of 1 to 20 carbon atoms;

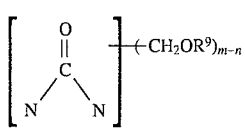
(d)

wherein $R^9$ is a linear or branched alkyl group of 1 to 20 carbon atoms;

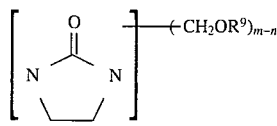
(e)

wherein $R^9$ is a linear or branched alkyl group of 1 to 20 carbon atoms;

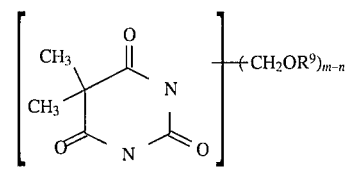
(f)

wherein $R^9$ is a linear or branched alkyl group of 1 to 20 carbon atoms;

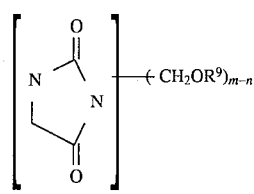
(g)

wherein $R^9$ is a linear or branched alkyl group of 1 to 20 carbon atoms;

(h) oligomeric aminoplast anchor molecules derived from self- or cross-condensation of any of (a) through (g) and mixtures thereof; and (i) mixtures of any of (a) through (h);

wherein m is at least 1; and wherein n is at least 0.5; and wherein $R^2$ is selected from the group consisting of hydrogen, alkyl of 1 to 20 carbon atoms, and aralkyl of 7 to 20 carbon atoms;

$R^3$ is selected from the group consisting of hydrogen, alkyl of 1 to 20 carbon atoms, aralkyl of 7 to 20 carbon atoms, and alkyl which is interrupted, substituted or interrupted and substituted by one or more oxygen, carbonyl, or carboxy groups;

$R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl which is interrupted, substituted, or interrupted and substituted by one or more oxygen, carbonyl, or carboxy groups; and $R^5$ is selected from the group consisting of hydrogen, alkyl of 1 to 20 carbon atoms, and aralkyl of 7 to 20 carbon atoms.

More specifically, the aryltriazine type aminoplast anchored stabilizers may be represented by the formula:

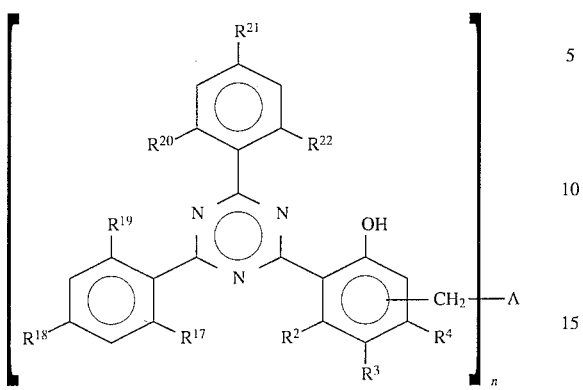

wherein
A is an m functional aminoplast anchor molecule to which n phenol rings are attached through n methylene bridges, said bridges replacing $R^3$, or $R^5$ groups on said phenol rings, which aminoplast anchor molecule is selected from the group consisting of:

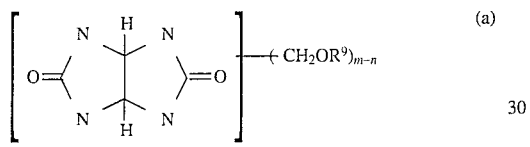

wherein $R^9$ is selected from the group consisting of methyl, ethyl, 1-propyl, 2-propyl, 1-butyl, 2-butyl, and mixtures thereof;

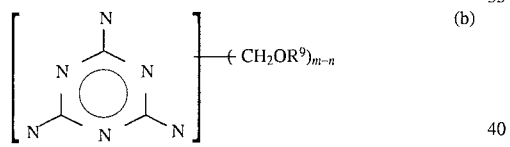

wherein $R^9$ is selected from the group consisting of methyl, ethyl, 1-propyl, 2-propyl, 1-butyl, 2-butyl, and mixtures thereof;

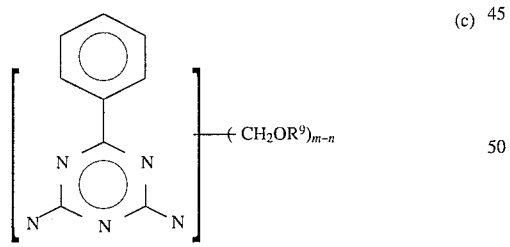

wherein $R^9$ is selected from the group consisting of methyl, ethyl, 1-propyl, 2-propyl, 1-butyl, 2-butyl, and mixtures thereof;
(d) oligomeric aminoplast anchor molecules derived from self- or cross-condensation of (a), (b), (c), or mixtures thereof; and
(e) mixtures of any of (a) through (d); wherein m is at least 1; and wherein n is at least 0.5; and
wherein
each of $R^{17}$ through $R^{22}$ is independently elected from the group consisting of alkyl of 1 to 20 carbon atoms, alkoxy of 1 to 20 carbon atoms, hydrogen, chloro, bromo, cyano, carboxy, and nitro groups;

wherein
$R^2$ is selected from the group consisting of hydrogen, alkyl of 1 to 20 carbon atoms, and aralkyl of 7 to 20 carbon atoms;
wherein
$R^3$ is selected from the group consisting of hydrogen, alkyl of 1 to 20 carbon atoms, aralkyl of 7 to 20 carbon atoms, and alkyl which is interrupted, substituted, or interrupted and substituted by one or more oxygen, carbonyl, or carboxy groups;
wherein
$R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl which is interrupted, substituted, or interrupted and substituted by one or more oxygen, carbonyl, or carboxy groups; and
wherein
$R^5$ is selected from the group consisting of hydrogen, alkyl of 1 to 20 carbon atoms, and aralkyl of 7 to 20 carbon atoms.

The preferred aryltriazine type aminoplast anchored stabilizers are those represented by the formula:

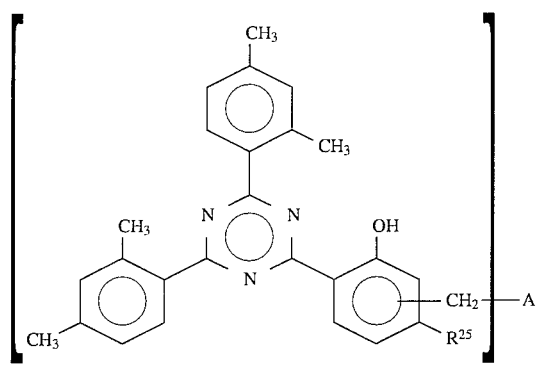

wherein
A is an m functional aminoplast anchor molecule to which n phenol rings are attached through n methylene bridges at a point of attachment ortho- or para- to the point of attachment of the hydroxy groups which aminoplast anchor molecule is selected from the group consisting of:

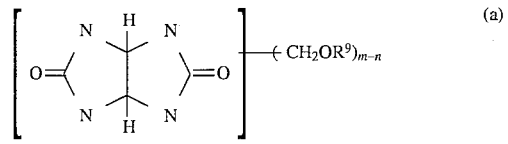

wherein $R^9$ is selected from the group consisting of methyl, ethyl, 1-propyl, 2-propyl, 1-butyl, 2-butyl, and mixtures thereof;

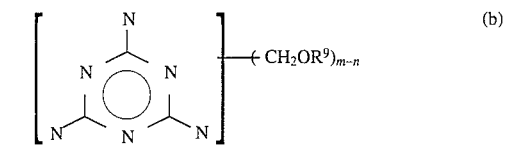

wherein $R^9$ is selected from the group consisting of methyl, ethyl, 1-propyl, 2-propyl, 1-butyl, 2-butyl, and mixtures thereof;

(c)

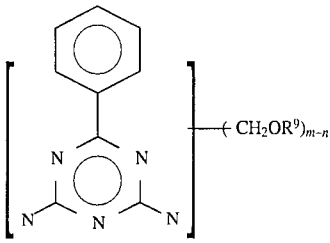

wherein $R^9$ is selected from the group consisting of methyl, ethyl, 1-propyl, 2-propyl, 1-butyl, 2-butyl, and mixtures thereof;

(d) oligomeric aminoplast anchor molecules derived from self- or cross- condensation of (a), (b), (c), or mixtures thereof; and (e) mixtures of any of (a) through (d);

wherein m is at least 1; and wherein n is more than 0.5; and wherein $R^{25}$ is selected from the group consisting of hydrogen, linear, branched or cyclic alkyl of 1 to 20 carbon atoms, and alkyl which is interrupted, substituted, or interrupted and substituted by one or more oxygen, carbonyl, and carboxy groups.

The preferred aminoplast anchor molecules are selected from the group consisting of:

(a)

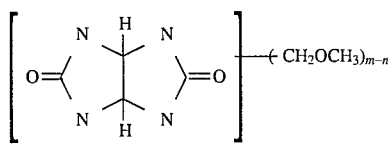

(b)

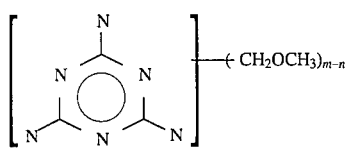

(c)

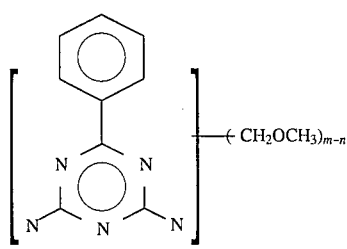

(d) oligomeric aminoplast anchor molecules derived from self- or cross-condensation of (a), (b), (c), or mixtures thereof; and (e) mixtures of any of (a) through (d).

An example of the preferred embodiment of the aryltriazine type stabilizers is represented by the formula:

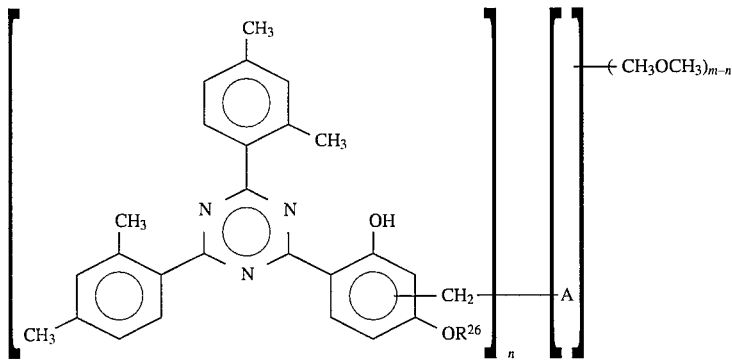

wherein A is a glycoluril anchor; and wherein $R^{26}$ is a linear, branched, or cyclic alkyl of 6 to 12 carbon atoms or mixtures thereof; wherein the methylene bridge is at a point of attachment ortho- or para- to the point of attachment of the hydroxy group; and wherein m is 2 to 14, and n is in the range of 1 to 14, wherein the ratio of hydroxyaryltriazines to glycolurils is from about 1:1 to about 4:1, and wherein the glycoluril is a mixture of monomeric, dimeric, trimeric, tetrameric, and higher oligomeric units.

AMINOPLAST ANCHORED BLOCKED OXANILIDE STABILIZERS

The blocked oxanilide UV stabilizers of the invention are represented by the formula:

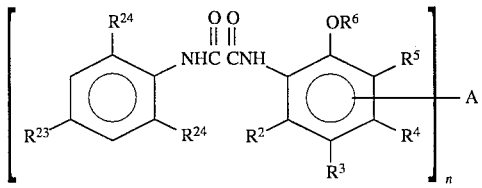

wherein

A is an m functional aminoplast anchor molecule to which n phenol rings are attached through n methylene bridges, said bridges replacing $R^3$, $R^4$, or $R^5$ groups on said phenol rings, which aminoplast anchor molecule is selected from the group consisting of:

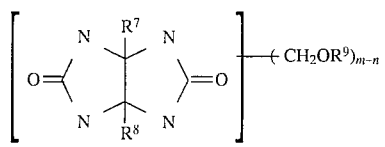 (a)

wherein $R^7$ and $R^8$ are independently selected from the group consisting of hydrogen, alkyl of 1 to 20 carbon atoms, aryl of 6 to 20 carbon atoms, and aralkyl of 7 to 20 carbon atoms; and wherein $R^9$ is a linear or branched alkyl group of 1 to 20 carbon atoms;

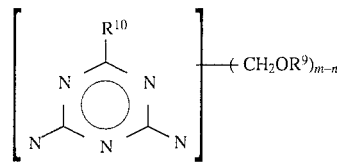 (b)

wherein $R^{10}$ is selected from the group consisting of alkyl of 1 to 20 carbon atoms, aryl of 6 to 20 carbon atoms, and aralkyl of 7 to 20 carbon atoms; and wherein $R^9$ is a linear or branched alkyl group of 1 to 20 carbon atoms;

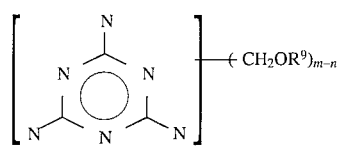 (c)

wherein $R^9$ is a linear or branched alkyl group of 1 to 20 carbon atoms;

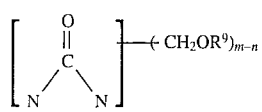 (d)

wherein $R^9$ is a linear or branched alkyl group of 1 to 20 carbon atoms;

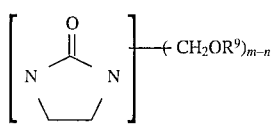 (e)

wherein $R^9$ is a linear or branched alkyl group of 1 to 20 carbon atoms;

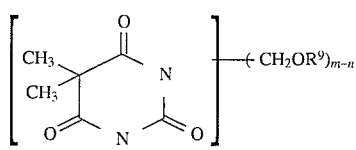 (f)

wherein $R^9$ is a linear or branched alkyl group of 1 to 20 carbon atoms;

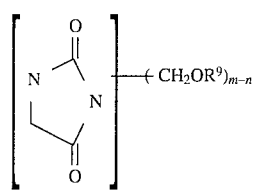 (g)

wherein $R^9$ is a linear or branched alkyl group of 1 to 20 carbon atoms;

(h) oligomeric aminoplast anchor molecules derived from self- or cross-condensation of any of (a) through (g) and mixtures thereof; and (i) mixtures of any of (a) through (h);

wherein m is at least 1; and wherein n is more than 0.5; and wherein each of $R^{23}$ and $R^{24}$ is the same or different and is independently selected from the group consisting of alkyl of 1 to 20 carbon atoms, aralkyl of 7 to 20 carbon atoms, alkoxy of 1 to 20 carbon atoms, hydrogen, chloro, bromo, cyano, and nitro groups;

wherein $R^2$ is selected from the group consisting of hydrogen, alkyl of 1 to 20 carbon atoms, and aralkyl of 7 to 20 carbon atoms;

$R^3$ is selected from the group consisting of hydrogen, alkyl of 1 to 20 carbon atoms, aralkyl of 7 to 20 carbon atoms, and alkyl of 1 to 20 carbon atoms which is interrupted, substituted, or interrupted and substituted by one or more oxygen, carbonyl, or carboxy groups;

$R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl of 1 to 20 carbon atoms which is interrupted, substituted, or interrupted and substituted by one or more oxygen, carbonyl, or carboxy groups;

$R^5$ is selected from the group consisting of hydrogen, alkyl of 1 to 20 carbon atoms, and aralkyl of 7 to 20 carbon atoms; and $R^6$ is a blocking group selected from the group consisting of alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

More specifically, the blocked oxanilide type aminoplast anchored stabilizers of the invention are represented by the formula:

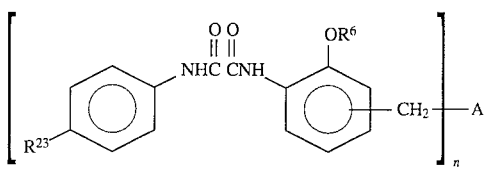

wherein

A is an m functional aminoplast anchor molecule to which n phenolic rings are attached through n methylene bridges, said bridges replacing hydrogen groups on said phenolic rings, which aminoplast anchor molecule is selected from the group consisting of:

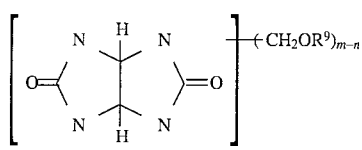 (a)

wherein $R^9$ is selected from the group consisting of methyl, ethyl, 1-propyl, 2-propyl, 1-butyl, 2-butyl, and mixtures thereof;

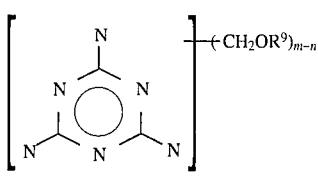

(b)

wherein $R^9$ is selected from the group consisting of methyl, ethyl, 1-propyl, 2-propyl, 1-butyl, 2-butyl, and mixtures thereof;

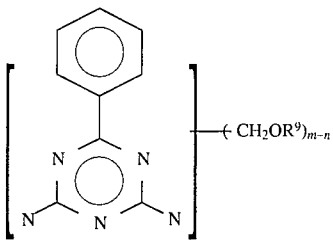

(c)

wherein $R^9$ is selected from the group consisting of methyl, ethyl, 1-propyl, 2-propyl, 1-butyl, 2-butyl, and mixtures thereof;

(d) oligomeric aminoplast anchor molecules derived from self- or cross-condensation of (a), (b), (c), or mixtures thereof; and (e) mixtures of any of (a) through (d);

wherein m is at least 1; and wherein n is more than 0.5; and wherein $R^{23}$ is selected from the group consisting of alkyl of 1 to 20 carbon atoms, aralkyl of 7 to 20 carbon atoms, alkoxy of 1 to 20 carbon atoms, hydrogen, chloro, bromo, cyano, and nitro groups; and $R^6$ is a blocking group selected from the group consisting of alkyl of 1 to 20 carbon atoms, acyl of 1 to 20 carbon atoms, alkylaminocarbonyl of 1 to 20 carbon atoms, arylaminocarbonyl of 6 to 20 carbon atoms, and trisubstituted silyl groups.

The preferred blocked oxanilide stabilizers of the invention are those wherein $R^6$ is selected from the group consisting of ethyl, acetyl, phenylaminocarbonyl, dodecylaminocarbonyl, and trimethylsilyl groups.

An example of the blocked oxanilide type stabilizers of the invention is represented by the formula:

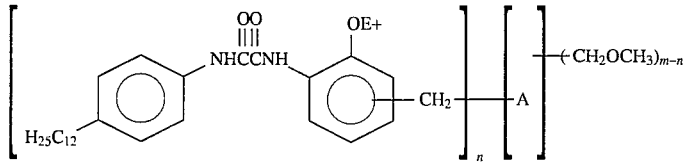

wherein A is a glycoluril anchor; and wherein m is 2 to 14 and n is in the range of from about 1 to about 14, wherein the methylene bridge is ortho-para-, or a mixture of ortho- and para- to the oxygen of the phenolic ring, wherein the ratio of oxanilide to glycoluril is from about 1:1 to about 4:1, and wherein the glycoluril is a mixture of monomeric, dimeric, trimeric, tetrameric, and higher oligomeric units.

PROCESS FOR PREPARATION

The aminoplast anchored monomeric or oligomeric stabilizers of the invention are prepared by contacting a monomeric or oligomeric aminoplast anchor A usable in this invention as described hereinabove in the section entitled "Aminoplast Anchors" with at least one blocked or unblocked phenolic stabilizer usable in the invention as described hereinabove in the section entitled "Phenolic Stabilizers" in a concentrated sulfuric acid reaction medium.

The novel process of the invention may employ any stabilizer to aminoplast ratio and is not restricted to the greater than 0.5:1 phenolic stabilizer to aminoplast ratio of the novel compositions of matter described previously in the section entitled "Anchored Products". Stabilizers having greater than 0.5:1 phenolic stabilizer to aminoplast ratios may certainly be prepared by the process of the invention, but stabilizers having less than 0.5:1 phenolic stabilizer to aminoplast ratios, such as a ratio of 0.01:1, may also be prepared by the process of the invention. The preferred stabilizer to aminoplast ratio is greater than 1:1, and the most preferred ratio is greater than 2:1.

The driving force for the acid catalyzed reaction between the reactants is the generation, from the alkoxymethylated or hydroxymethylated aminoplast reactant, of a positively charged electrophilic center on the methylene group of the alkoxymethyl or hydroxymethyl attached to the aminoplast by elimination of the elements of an alcohol or water from a protonated aminoplast. The positively charged electrophilic center then produces an anchored stabilizer of the invention by an electrophilic aromatic substitution reaction at the most electron rich, unblocked center of the phenolic stabilizer, usually ortho- or para- to the phenolic oxygen, or a mixture thereof. When a reactive ortho- site is blocked with a substituent group, then the para-position is attacked by the electrophile. When both ortho- and para-positions are blocked by substituent groups, then an unblocked position meta- to the phenolic oxygen may be substituted. In general, the aromatic hydrogens are the most easily substituted moieties on the phenol ring. However, other labile groups such as tertiary butyl and tertiary octyl groups may also be electrophilically substituted. When, in addition to the phenolic oxygen, a multiplicity of substituents are present on the phenolic ring, some being electron releasing and others being electron withdrawing, then the sum of all effects will determine the electrophilic aromatic substitution reaction site on the phenolic ring in accordance with the well established principles of orientation in electrophilic aromatic substitution chemistry. Some of the basic principles of electrophilic aromatic substitution chemistry are described by R. O. C. Norman in "Principles of Organic Synthesis", 2nd Edition, Chapman and Hall, London (1978), in the chapter entitled "Electrophilic Aromatic Substitution" under the heading "Directire and Rate Controlling Factors", pages 370 to 377.

Alkoxymethylated aminoplasts are known to undergo self condensation reactions when exposed to acids, and particularly when exposed to acids and heat. The product of the self condensation reaction is an oligomeric alkoxymethylated aminoplast if the starting aminoplast is monomeric. Similarly, if the starting aminoplast is oligomeric, then higher oligomers are produced by the self condensation reaction.

It is the surprising discovery of this invention that when the acid used in the process of the invention is concentrated sulfuric acid, and particularly when concentrated sulfuric acid is used as the reaction medium in which the aminoplast anchor is contacted with the phenolic stabilizer, the expected self-condensation reaction of the aminoplasts is suppressed such that only relatively low levels of oligomeric products result.

As a consequence of suppressed self-condensation, the aminoplast anchored stabilizers prepared by the process of this invention comprise, in addition to the monomers, only lower oligomeric components such as dimers, trimers, and occasionally tetramers. While it is possible, in very rare cases, to obtain higher oligomers, oligomers higher than tetramers generally are not obtained. By varying the reaction conditions, however, it is possible to control the degree of oligomerization to produce higher or lower oligomeric anchored stabilizers.

Because the self condensation reaction of alkoxymethylated aminoplasts proceeds concurrently and competitively with the electrophilic aromatic substitution reaction on the phenolic stabilizers, products with varying degrees of oligomerization may be obtained depending on the reaction condition, particularly the mode of addition of reactants used in the process of the invention. Thus, adding the phenolic stabilizer reactant to a mixture of the alkoxymethylated aminoplast and acid will produce a product more highly oligomeric than employing a mode of addition wherein an alkoxymethylated aminoplast is gradually added to a mixture of the phenolic stabilizer reactant and the acid. The mode of addition wherein the aminoplast is added to the remaining ingredients produces the least amount of oligomeric products. The product therefore has an overall low degree of oligomerization.

A mode of addition wherein the acid is added to a mixture of the aminoplast and the phenolic stabilizer reactants will have an intermediate degree of oligomerization.

The reaction is conducted by contacting the named reactants in any convenient manner in liquid concentrated sulfuric acid reaction medium having a sulfuric acid concentration of at least 75 weight percent.

The reaction may be conducted as a batch or as a continuous process at the convenience of the operator. The number of moles of the phenolic stabilizer per each aminoplast alkoxymethyl group in the product is typically in the range of from 0.01:1 to 1.2:1. The anchored product may be isolated by precipitation from cold water or it may be extracted with an organic solvent by known techniques.

The process of the invention comprises contacting an alkoxymethylated aminoplast with a phenolic stabilizer in the presence of sulfuric acid as the reaction medium at a temperature and for a length of time sufficient to produce the novel monomeric or oligomeric aminoplast anchored stabilizers of the invention.

The process is carried out typically at a temperature in the range of −15° C. to 50° C., although temperatures which are lower or higher may also be used. The preferred temperature, however, is from about 0° C. to about 26° C.

The process is carried out for a period of time typically in the range of from about 5 minutes to about 5 hours, although shorter or longer periods may also be used. The preferred time, however, is from about 30 minutes to about 3 hours.

CURABLE COMPOSITION

The novel compositions of matter described above are useful as ultraviolet (UV) stabilizer additives to polymers, particularly as additives to thermoplastic polymers and thermoset systems. They may be added to the polymer to impart useful stabilizing properties to the polymer by themselves or in combination with antioxidant or hindered amine stabilizers.

In thermoplastic polymer applications stabilizing polymers such as polyethylene, polypropylene, polyvinylchloride, polystyrene, polycarbonates, polyurethanes, polyamides, and the like, the novel aminoplast anchored stabilizers of the invention are simply incorporated into thermoplastic materials at a level in the range of about 0.01 to about 5 weight percent by methods known in the art.

In thermoset coating applications, the aminoplast anchored stabilizers of the invention are used to prepare a novel curable composition which composition is thereafter cured to produce light stable films and objects.

The novel curable composition of the invention comprises:

(i) a stabilizingly effective amount of a stabilizer comprising an aminoplast anchor having more than 0.5 mole of phenolic stabilizer group per mole of aminoplast pendently attached thereto;

(ii) a crosslinkingly effective amount of a crosslinking agent; and (iii) a polyfunctional, active hydrogen containing material.

The preferred curable compositions comprise a stabilizer (i), which is a stabilizer of the invention, in an amount of at least 0.01 weight percent of the total weight of the curable composition.

Typically, the novel curable composition of the invention comprises:

(i) about 0.01 to 5 weight percent of a novel stabilizer of the invention;

(ii) about 3 to 55 weight percent of a crosslinking agent; and (iii) about 40 to 97 weight percent of a polyfunctional active hydrogen containing material.

The curable composition, optionally, may contain a cure catalyst to accelerate curing.

The novel stabilizers of the invention are described hereinabove in the section entitled "Anchored Products". They may be blocked or unblocked, monomeric or oligomeric, or they may be mixtures.

The crosslinking agent may be an aminoplast crosslinking agent selected from unetherified, partially etherified or fully etherified aminoplast resins, or it may be any mixture thereof.

The aminoplast crosslinkers are described above in the section entitled "Aminoplast Anchors" and include crosslinkers such as CYMEL® 1130 resin, CYMEL® 303 resin, CYMEL® 1170 resin, POWDERLINK® 1174 resin, CYMEL® 1123 resin, and the like.

The polyfunctional active hydrogen containing material comprises at least one class of active hydrogen functionality selected from the group consisting of carboxy, hydroxy, amido, mercapto, and a group convertible thereto. The hydroxy and carboxy functional groups are preferred.

Especially suitable polyfunctional active hydrogen containing materials include polyesters, polyacrylates, polyurethane polyols, and products of condensation of amines with epoxy resins, all containing hydroxy groups as reaction sites. The polyesters are obtained in a known manner by, for example, the reaction of polyfunctional carboxylic acids with excess quantities of polyhydric alcohols; the polyacrylates are obtained by the copolymerization of acrylic or methacrylic acid derivatives with hydroxy group containing derivatives of these acids, such as, for example, the hydroxy-alkyl esters, optionally with the simultaneous use of additional vinyl compounds, such as, for example, styrene. The hydroxy group containing polyurethanes can be obtained, in a known manner, by the reaction of polyisocyanates with excess quantities of compounds containing at least two hydroxy groups.

Suitable commercially available hydroxy group containing polyesters are CYPLEX® 1531, a polyester of phthalic acid, adipic acid, ethanediol, and trimethylol propane from American Cyanamid Company, Cargil Polyester 5776, available from Cargil, and TONE® 0200 available from Union Carbide Corp. Suitable hydroxy functional acrylic resins are available commercially from S. C. Johnson & Son, Inc. under the trademark JONCRYL® 500, a copolymer of styrene, hydroxypropyl methacrylate and butyl acrylate, and from Rohm & Haas Co. under the trademark AT-400. Also suitable for use are hydroxy-terminated polycaprolactones.

The hydroxyfunctional polyfunctional active hydrogen containing material comprises compounds and resins selected from acrylic resins, polyester resins, polyurethanes, polyols, products derived from the condensation of epoxy resins with amines, and mixtures thereof.

A cure catalyst to accelerate the crosslinking reaction may be also optionally used, however, the curable compositions of the invention are capable of curing without an added catalyst.

When a catalyst is present, crosslinking takes place more rapidly at a particular temperature than when a catalyst is not present. Typically, crosslinking is effected at a lower temperature with a catalyst present.

The acid cure catalysts usable in the invention include carboxylic acids such as phthalic and oxalic acids; sulfonic acids such as para-toluenesulfonic acid, dinonyl naphthalenesulfonic acid, naphthalene sulfonic acid, dodecylbenzenesulfonic acid; phosphonic acids; mineral acids such as nitric acid, sulfuric acid, phosphoric acid, polyphosphoric acid, and the like. The use of a sulfonic acid is preferred.

When employed, the cure catalyst is used in the curable compositions of the invention in amounts effective to accelerate cure at the temperature employed. For example, the catalyst is typically used in amounts of from about 0.01 to about 2.0% by weight, with 0.02 of 1% by weight, based on the weight of the curable compositions, being preferred.

In the practice of the invention, the curable compositions can be adapted for use in solvent-based, water-based, and powder coating applications. They may also be used in molding applications. Sulfonimide catalysts are particularly well suited for use in powder coating applications.

The curable compositions of the invention may also contain other stabilizers such as monomeric or oligomeric hindered amine light stabilizers (HALS), phenolic antioxidants, phosphite antioxidants, sulfur containing antioxidants such as sulfides and disulfides, other UV absorbers, acid scavengers, fillers, pigments, flame retardants, and the like.

METHOD OF USING

This invention is also an improved method of using the aminoplast anchored novel stabilizers of the invention described above in the section entitled "Anchored Products." The method utilizes the novel curable compositions of the invention also described above in the section entitled "Curable Compositions."

The novel method described herein is an improved method of coating substrates of the type having the steps of (I) contacting said substrate with a conventional curable composition containing a stabilizer, a crosslinking agent, and a polyfunctional active hydrogen containing material, and (II) thereafter curing said conventional curable composition, wherein the improvement comprises:

(a) contacting said substrate with a novel curable composition comprising:
  (i) a stabilizingly effective amount of a stabilizer comprising an aminoplast anchor having more than 0.5 mole of phenolic stabilizer group per mole of aminoplast pendently attached thereto;
  (ii) a crosslinkingly effective amount of a crosslinking agent; and
  (iii) a polyfunctional active hydrogen containing material; and
(b) thereafter curing said novel curable composition. The substrate to be coated may be selected from surfaces such as steel, aluminum, plastic materials, and the like. Alternatively, a mold may be used instead of a surface to practice the method of the invention.

The contacting of a substrate with the novel curable composition of the invention may be carried out by any of the conventional coating methods including spraying, padding, brushing, electrostatic spraying as is the case in powder coatings, roller coating, curtain coating, flow coating, dipping, and electrocoating.

The curing may be carried out by continued application of heat at an elevated temperature or at an ambient temperature.

The cure may be accelerated by the use of a suitable catalyst such as those used to cure the novel curable compositions.

STABILIZED ARTICLES

The novel method of using the anchored stabilizers of the invention according to the method described above produce a product, which, in this case, is a crosslinked article in the form of a film such as coatings, or it is in the form of an article such as a molded product.

The cured compositions may be used as coatings for wire, appliances, automotive parts, furniture, pipes, machinery, and the like. Surfaces which are suitable include plastics, wood, and metals such as steel, aluminum, and the like.

The cured compositions may also be used to form solid articles such as cases, enclosures, and structural members.

The following examples illustrate the preparation and use of the novel stabilizers of the invention by the process of the invention. These examples are not, however, intended to limit the claims in any manner whatsoever.

EXAMPLE 1

Recrystallized solid POWDERLINK® 1174 resin* having the chemical name tetramethoxymethyl glycoluril (8.0 g, 0.025 mole) was added, over a period of 20 minutes, to a mixture of cooled (10° C.) and vigorously stirred solution of CYASORB® UV 5411 ultraviolet light stabilizer** having the chemical name of 2-(2-hydroxy-5-tertiary-octylphenyl)benzotriazole (32.2 g, 0.1 mole) and 98% sulfuric acid (90 ml) under a nitrogen blanket, while maintaining the temperature of the reaction mixture at 12° to 16° range. After the addition was complete, the temperature of the reaction mixture was allowed to rise to 23° C. over a period of 45 minutes and when then kept at ambient temperature for an additional 80 minutes. The resulting reddish to orange colored solution was poured onto cold (0° C.) water (500 ml) with vigorous, high shear agitation. The light yellow colored, finely dispersed solid precipitate was collected by filtration and washed with cold water or dilute aqueous sodium bicarbonate and then with cold methanol containing 10 weight percent water. The washing steps were repeated until a 15 weight percent solution of the product in xylenes had a clear appearance indicating that the product was essentially free of salt impurities.

*POWDERLINK® 1174 powder aminoplast resin, a product of American Cyanamid Company, Wayne, N.J., is a substantially fully methoxymethylated and highly monomeric glycoluril resin having an average molecular weight of about 350 and equivalent weight in the range of from 90 to 125.7.
**CYASORB® UV 5411 light stabilizer, a product of American Cyanamid Company, Wayne, N.J., is a benzotriazole type ultraviolet light absorber.

After drying at 70° C. under reduced pressure, a light tan colored, fine, powdery material was obtained in near quantitative yield (39.8 g). The following characteristics were determined experimentally:

(1) The product was readily soluble in organic solvents such as toluene, xylene, tetrahydrofuran, and dimethylsulfoxide.
(2) The product was soluble in amino resins such as CYMEL® 1133 resin*, at a level of at least 20 weight percent. Preparation of even a 10 weight percent solution of 2-(2-hydroxy-5-tertiaryoctylphenyl)benzotriazole, in contrast, was possible only when the mixture of the triazole and CYMEL® 1133 resin was heated. Upon cooling to room temperature, however, 2-(2-hydroxy-5-tertiaryoctylphenyl)benzotriazole crystallized out of the solution, indicating incompatibility with CYMEL® 1133 resin which is a typical melamine-formaldehyde resin used extensively in coatings. It is concluded from the above comparison of solubility behavior of the aminoplast anchored benzotriazole with its unanchored precursor that the compatibility of a benzotriazole is substantially increased by anchoring said benzotriazole onto an aminoplast anchor molecule.
*CYMEL® 1133 is a highly alkoxymethylated liquid melamine resin having mixed alkyl groups comprising methyl and n-butyl groups in about a 1:1 molar ratio.
(3) The product was free of tetramethoxymethylglycoluril starting material as indicated by High Performance Size Exclusion Chromatography (HPSEC) tracing experiments.
(4) The product contained 1.6 percent by weight unreacted 2-(2-hydroxy-5-tertiaryoctylphenyl)benzotriazole starting material as indicated by HPSEC tracing experiments.
(5) The product comprised monomeric, dimeric, trimeric, and tetrameric components as indicated by an excellent agreement between the measured molecular weight as determined by Vapor Phase Osmometry (VPO) and the molecular weight calculated by taking into account the relative contributions of each component present in the product according to their relative peak areas in the HPSEC output.
(6) The product had a benzotriazole to methoxymethyl molar ratio of 50:1 as determined by Nuclear Magnetic Resonance Spectroscopy (NMR) indicating greater than 98% conversion of the methoxymethyl groups to methylene bridge groups.
(7) The product exhibited a strong infrared absorption band at 875 cm$^{-1}$, an absorption far greater in intensity than the starting benzotriazole absorption in the same region. The 875 cm$^{-1}$ absorption in the aminoplast anchored product is assigned to the two hydrogens meta- to the hydroxy group, whereas in the starting benzotriazole, the strong band at 820 cm$^{-1}$ is assigned to two adjacent hydrogens on the phenol ring (viz. ortho- and meta- to the hydroxy group). It is concluded from the above observations in the infrared spectrum of the starting material and the reaction product, that reaction had indeed occurred between the methoxymethyl group of the glycoluril and the phenol ring of the benzotriazole, forming a new C—C bond at the position ortho- to the phenolic hydroxy. The above conclusion is further supported by the complete disappearance of the 820 cm$^{-1}$ absorption band, present in the starting benzotriazole, from the infrared spectrum of the product which no longer has adjacent hydrogens.
(8) The product also exhibited, in its ultraviolet spectrum, a bathochromic shift, 6 nano-meters in magnitude, to longer wavelengths relative to the starting benzotriazole: 303 nm in the product, versus the 297 nm in the starting material, as expected on the basis of an ortho-methylene bridging. Based on the above facts and observations, we conclude that the data presented above provide clear and convincing proof in support of the structure suggested for the novel aminoplast anchored stabilizers of the invention.

EXAMPLE 2

The procedure of Example 1 was repeated using 9.5 g of CYMEL® 1171 resin*, a product of American Cyanamid Company, Wayne, N.J., instead of the tetramethoxymethylglycoluril resin (POWDERLINK® 1174) used in Example 1, with the exception that the salt impurities were removed by reslurrying the product in water (600 ml) at ambient temperatures, with vigorous agitation for about 1 hour, filtering, and repeating the reslurrying step at 80° to 85° C. and filtering to give, after drying, a glycoluril anchored benzotriazole stabilizer in near quantitative yield (36.1 g). The product was very similar to the product obtained in the procedure of Example 1. It had the following additional characteristics:
*CYMEL® 1171 resin is a highly alkoxymethylated glycoluril resin having mixed alkyl groups consisting of methyl and ethyl groups in about 1:1 molar ratio.
(1) The product contained 0.7 weight percent unreacted 2-(2-hydroxy-5-tertiaryoctylphenyl)benzotriazole starting material as determined by HPSEC.
(2) The product contained 1.2 weight percent unreacted CYMEL® 1171 resin as determined by HPSEC.
(3) The product exhibited a thermogravimetric volatility profile (TGA) indicative of 5% weight loss on heating to 300° C.
(4) The product had a total acidity of 0.15 milliequivalent per gram of product as determined by potentiometric titration.

This example illustrates the preparation of another glycoluril anchored benzotriazole stabilizer of the invention using mixed alkoxyalkylglycoluril as the starting aminoplast anchor molecule.

EXAMPLE 3

The procedure of Example 1 was repeated using 12.5 g of CYMEL® 300 resin,* a product of American Cyanamid Company, Wayne, N.J., instead of the POWDERLINK® 1174 resin, with the exception that the filtered product was:
*CYMEL® 300 resin is a highly methoxymethylated melamine resin having a degree of polymerization of about 1.35, corresponding to about 80% monomer.
(1) washed with dilute aqueous sodium bicarbonate solution,
(2) slurried in an 8:2 ratio of a methanol-water mixture (400 ml),
(3) agitated at room temperature for about 3.5 hours,
(4) after filtering and drying as described in Example 1, it was redissolved in xylenes and the insoluble salts were removed by filtration, and
(5) the xylenes were removed by distillation under reduced pressure.

The residue was a melamine anchored benzotriazole stabilizer, an example of the novel stabilizers of the invention.

The product contained about 2 weight percent of unreacted CYASORB® UV 5411 stabilizer as determined by HPSEC.

EXAMPLE 4

The procedure of Example 1 was repeated using 19.6 g of CYMEL® 1123 resin*, a product of American Cyanamid Company, Wayne, N.J., instead of the POWDERLINK® 1174 resin, with the exception that the filtered product was washed several times with dilute aqueous sodium bicarbonate solution. Analysis of the product at this stage by HPSEC indicated that no benzotriazole starting material was present. There was present, however, about 3.5 weight percent unreacted CYMEL® 1123 resin.

*CYMEL® 1123 resin is a highly alkoxymethylated benzoguanamine resin having mixed alkyl groups consisting of methyl and n-butyl groups.

The crude product was further purified by reslurrying the product in 87.5 weight percent aqueous methanol (400 ml) with agitation at room temperature for 5 hours. Filtering, washing with methanol, and drying gave a light tan colored powder (41.4 g) having a total acidity of 0.23 milliequivalent per gram of product as determined by potentiometric titration.

EXAMPLE 5

The procedure of Example 1 was repeated using half the amount of POWDERLINK® 1174 resin (4.0 g, 0.0125 mole) with the exception that CYASORB®UV 1164 stabilizer* (2.5.5g, 0.050 mole) was used instead of CYASORB® UV 5411.

*CYASORB® UV 1164 stabilizer, a product of American Cyanamid Company, Wayne, N.J., is an orthohydroxy- aryltriazine ultraviolet light absorber having the chemical name 2,4-di-(2,4-dimethylphenyl)-6-(2-hydroxy-4-normaloctoxyphenyl)-1,3,5-triazine.

The crude reaction product contained 1.1 weight percent unreacted CYASORB® UV 1164 stabilizer as determined by HPSEC. To further purify the product, the crude product was reslurried in 90 weight percent aqueous methanol (400 ml) with agitation for 1.5 hours at room temperature, filtered, and dried to give a light yellow powder (29.8 g) having a total acidity of 0.23 milliequivalent per gram as determined by potentiometric titration.

The product was soluble in CYMEL® 1133 resin at room temperature at a 10 weight percent level producing clear solutions. In contrast, the starting CYASORB® UV 1164 stabilizer gave turbid solutions even at the lower, 5 weight percent levels. This demonstrates the increased compatibility of the aminoplast anchored CYANSORB® UV 1164 stabilizer of the invention over its precursor in a coating system such as CYMEL® 1133, which is a typical melamine resin widely used in coatings.

EXAMPLE 6

The procedure of Example 1 was repeated using:
(1) CYASORB® 1164 stabilizer (51.0 g, 0.10 mole) instead of CYASORB® UV 5411, and
(2) using CYMEL® 1171 resin (9.5 g) instead of the POWDERLINK® 1174 resin.

The crude reaction product was reslurried in water, and then dilute aqueous sodium bicarbonate was added, then stirred, the solids filtered, and washed. The purification cycle was repeated to give a dried product (54.3 g) having a total acidity of 0.17 milliequivalent per gram as determined by potentiometric titration. The product contained 1.1 weight percent unreacted starting CYASORB® UV 1164 stabilizer as determined by HPSEC.

EXAMPLE 7

The procedure of Example 1 was repeated using CYASORB® UV 531 stabilizer* (32.6 g, 0.10 mole) instead of CYASORB® UV 5411 stabilizer. The washed product melted during the drying step but resolidified upon cooling to give a yellow, brittle mass which was readily soluble in organic solvents such as acetone, tetrahydrofuran, xylenes, and toluene, but only partially soluble in methanol or higher alcohols. The product had total acidity of 0.19 milliequivalent per gram of product as determined by potentiometric titration. The product also contained a small amount (less than 0.5 weight percent) of unreacted CYASORB® UV 531 stabilizer as determined by HPSEC.

*CYASORB® UV 531 stabilizer, a product of American Cyanamid Company, Wayne, N.J., is a benzophenone type UV stabilizer having the chemical name 2-hydroxy-4-hydroxy-4-normaloctoxybenzophenone.

The product was further purified by dissolving in xylenes and adding hexane to precipitate the glycoluril anchored 4-n-octoxy-2-hydroxybenzophenone stabilizer of the invention.

EXAMPLE 8

The procedure of Example 1 was repeated using CYASORB® UV 531 stabilizer (32.69, 0.10 mole) instead of CYASORB® UV 5411, and using CYMEL® 300 resin (8.2 g) instead of the POWDERLINK® 1174 resin. After washing, bicarbonate treatment, and reslurrying several times, the yellow product solidified on cooling to a brittle mass. The product contained no starting CYASORB® UV 531 stabilizer, but a small amount (less than 1 weight percent) of unreacted CYMEL® 300 resin was detected by HPSEC.

EXAMPLE 9

To cooled (ice bath) concentrated sulfuric acid (80 ml) in a 250 ml three neck flask equipped with a thermometer, agitator and nitrogen inlet, 45.29 (0.1 m) of SANDOVUR® 3206 oxanilide absorber, a product of Sandoz Corp., was added over a period of 10 minutes at 6° to 12° C. temperature range with stirring. CYMEL® 1171 resin 9.8 g (0.031 m) was then added over a period of 10 minutes while maintaining a temperature in the 8° to 16° C. range. The reaction mixture was kept at 15°–17° C. for 50 minutes, and then the temperature was allowed to rise to 25° C., and the mixture was allowed to stand for another 50 minutes. The product was precipitated by pouring the reaction mixture over 500 g of ice water under vigorous agitation. After cold and hot water extractions, the product was collected and dried under reduced pressure at 85° C. High Performance Size Exclusion Chromotography (HPSEC) revealed the presence of four major fractions, attributed to monomeric (16%), dimeric (8%), trimeric (54%), tetrameric (17%), and higher oligomeric (5%) components. The Fourier-Transform Infrared Spectrum (FTIR) indicated that the electrophilic substitution had taken place in the ortho- and para-positions relative to the point of attachment of the ethoxy groups in about 40:60 ratio.

EXAMPLE 10

POWDERLINK® 1174 resin (0.8 g, 0.0025 mole) was added to a mixture of salicylic acid (1.38 g, 0.010 mole) and concentrated sulfuric acid (14 ml) at about 15° C. The mixture was then allowed to warm to room temperature overnight and then poured over ice water (100 g) to give a white precipitate which was collected by filtration to give a product (76% yield) which contained the methylene bridged adducts.

EXAMPLE 11

The procedure of Example 1 is repeated with the exception that instead of the 0.1 mole of CYASORB® UV 5411 stabilizer reactant used in Example 1, a mixture of CYASORB® UV 5411 (16.1 g, 0.05 mole) and CYASORB® UV 531 (16.3 g, 0.05 mole) is used as the stabilizer reactant. POWDERLINK® 1174 (8.0 g, 0.025 mole) is used as the aminoplast reactant. The product obtained contains a POWDERLINK® 1174 anchored stabilizer wherein the pendant stabilizer group is a mixture of CYASORB® UV 5411 and CYASORB® UV 531 stabilizers present in approximately equimolar quantities.

EXAMPLE 12

A set of six white pigmented acrylic based coat-clear coat panels were prepared using CYMEL® 1130 resin as the crosslinking agent using the following conditions:

| PIGMENTED BASE COAT | |
|---|---|
| Acryloid ® AT-400/CYMEL ® 1130 Ratio | 60/40 |
| OR-650 Pigment/Binder Ratio | 0.8 |
| para-Toluenesulfonic Acid, Weight % on TRS (total resin solids) | 0.4 |
| normal Butanol, Weight % on TRS | 20 |
| Non-Volatiles, weight % (Xylene makeup) | 65 |
| Substrate | BO 100 CRS |
| Schedule | 20 min/100° C. |
| CLEAR COAT | |
| ACRYLOID ® AT-400/CYMEL ® 1130 Ratio | 60/40 |
| para-Toluensulfonic Acid, Weight % on TRS | 0.3 |
| normal Butanol, Weight % on TRS | 20 |
| Xylene Make-up Containing Test Stabilizers Non-volatiles, Weight % | 65 |
| Film Thickness (#46 Applicator), mils | 1.75 |
| mm | 0.044 |
| Schedules, Standard | 30 min/121° C. |
| Overbake | Standard Plus 30 min/177° C. |

The test stabilizers were added as 18 weight % solutions in xylene to the fully formulated clear coat composition at a 6 weight percent loading of "active" CYASORB® UV 5411 based on CYMEL® 1130 resin solely. The test stabilizers used and the base coat/clear coat cured coatings derived therefrom by curing under normal and overbake conditions are listed below:

| AMINOPLAST ANCHORED STABILIZERS | COATINGS | |
|---|---|---|
| | NORMAL | OVERBAKE |
| (1) CYASORB ® UV 5411/ POWDERLINK ® 1171 (3:1 Ratio)* | A | G |
| (2) CYASORB ® UV 5411/ POWDERLINK ® 1174 (4:1 Ratio)* | B | H |
| (3) CYASORB ® UV 5411/ CYMEL ® 300 (3:1 Ratio)* | C | I |
| (4) CYASORB ® UV 5411/ CYMEL ® 1123 (3.8:1 Ratio)* | D | J |
| (5) CYASORB ® UV 5411 (Control) Stabilizer | E | K |
| (6) No Stabilizer Additives (Blank) | F | L |

*Molar Ratios.

Coatings A through J were exposed to ultraviolet light in a QUV unit, available from Q-Panel Company, Cleveland, Ohio, for the purpose of carrying out an accelerated exposure test. The QUV data was generated at 8 hours UV exposure at 70° C., followed by 4 hours condensation at 50° C. cycle, hereinafter "GM Cycle." The test was terminated after 2500 hours total time.

Examination of the QUV exposed coatings with respect to gloss, yellow index, distinctness of image (DOI), and cracking (see Table 1) revealed that coatings G and H did not exhibit any cracking under GM cycle. Coatings G and H outperformed all others in the overbake series, with coating H outperforming coating G. Under overbake conditions, coating K was the worst, except for coating L (blank) which was not stabilized. In the case of coating K, CYASORB® UV 5411, being volatile, was depleted during overbake.

In the normal series, coating E outperformed only coating D by a slight margin. Coatings A, B, and C all outperformed coating E, with coating B outperforming all others in gloss, yellow index, distinctness of image (DOI), and cracking.

It is concluded from the QUV exposure data (Table 1) that:

(1) aminoplast anchored stabilizers are superior to their unanchored precursors, particularly under overbake conditions, due to their reduced volatility as a result of increased molecular weight;
(2) POWDERLINK® 1174 anchored stabilizers are superior to all others;
(3) anchored stabilizers having high stabilizer/aminoplast ratios are superior to those having lower ratios even when used at identical "active" stabilizer levels; and
(4) anchored stabilizers have superior permanence in the film than their unanchored precursors under normal and overbake conditions. This is manifested by a 100% ultraviolet absorption retention of coatings B and H versus only 30% absorption retention of coating E (normal bake conditions) and 0% absorption retention of coating K (overbake conditions).

TABLE 1

QUV EXPOSURE BEHAVIOR OF AMINOPLAST
ANCHORED CYASORB ® UV 5411 STABILIZED
BASE COAT/CLEAR COAT COATINGS

| COATINGS | 20° Gloss % | | Distinctiveness of Image % | | Yellow Index | | | Cracking Rating | |
|---|---|---|---|---|---|---|---|---|---|
| | Initial | Final | Initial | Final | Initial | Final | | | |
| | O HR | 2457 HR | O HR | 2457 HR | O HR | 2457 HR | Change | Initial | Final |
| NORMAL BAKE | | | | | | | | | |
| A | 93.2 | 99 | 92.9 | 99 | −2.10 | +7.7 | 9.8 | 0 | 0 |
| B | 93.4 | 96 | 94.8 | 96 | −2.21 | +6.8 | 9.0 | 0 | 0 |
| C | 93.0 | 88 | 90.5 | 88 | −1.16 | +12.0 | 13.2 | 0 | 2 |
| D | 93.5 | 57 | 95.6 | 47 | −1.77 | +13.2 | 15.0 | 0 | 5 |
| E | 93.3 | 62 | 92.1 | 62 | −3.11 | +13.5 | 16.6 | 0 | 4 |
| F | 92.6 | 3 | 92.9 | 0 | −3.3 | +23.5 | 26.8 | 0 | 5 |
| OVERBAKE | | | | | | | | | |
| G | 97.6 | 94 | 93.6 | 62 | +0.26 | +9.2 | 8.9 | 0 | 0 |
| H | 97.5 | 95 | 92.1 | 71 | +0.02 | +8.7 | 8.7 | 0 | 0 |
| I | 97.1 | 78 | 86.3 | 43 | +1.70 | +14.5 | 12.8 | 0 | 3 |
| J | 97.4 | 44 | 91.6 | 33 | +0.78 | +15.3 | 14.5 | 0 | 5 |
| K | 96.4 | 6 | 90.8 | 0 | −2.05 | +19.7 | 21.8 | 0 | 5 |
| L | 96.5 | 3 | 91.0 | 0 | −2.75 | +24.9 | 27.7 | 0 | 5 |

Although the present invention has been described with reference to certain preferred embodiments, it is apparent that modifications and variations thereof may be made by those skilled in the art without departing from the scope of this invention as defined by the appended claims.

We claim:

1. A method of coating a substrate comprising the steps of (I) contacting said substrate with a curable composition comprising (i) a stabilizingly effective amount of a stabilizer composition, (ii) a crosslinkingly effective amount of a crosslinking agent, and (iii) a polyfunctional active hydrogen containing material, and (II) thereafter curing said curable composition, wherein the stabilizer composition comprises a monomeric or oligomeric aminoplast anchor having more than 0.5 mole of phenolic light stabilizer groups per mole of aminoplast pendently attached thereto via an N-methylene bridge, represented by the formula

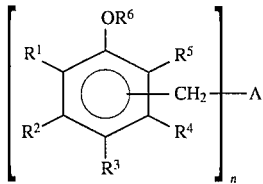

wherein

A is an m functional monomeric or oligomeric aminoplast anchor molecule to which n phenolic light stabilizer groups are attached through n N-methylene bridges, the bridges replacing the $R^2$, $R^3$, $R^4$ or $R^5$ groups on the phenolic ring;

$R^1$ is a group which, together with the phenolic ring, comprise the phenolic light stabilizer group;

$R^2$, $R^3$, $R^4$ and $R^5$ are substituents independently selected from the group consisting of hydrogen, alkyl, aryl, aralkyl, hydroxy, alkoxy, and alkyl which is interrupted, substituted, or interrupted and substituted by one or more oxygen, carbonyl or carboxy groups;

$R^6$ is hydrogen or a blocking group selected from the group consisting of alkyl, acyl, aminocarbonyl and silyl groups;

m is at least 1; and n is more than 0.5.

2. The method as recited in claim 1, wherein the aminoplast anchor is selected from the group consisting of

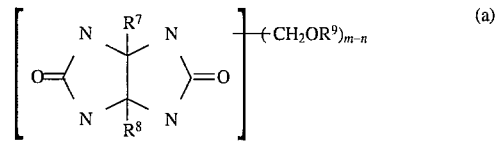

wherein $R^7$ and $R^8$ are independently selected from the group consisting of hydrogen, alkyl of 1 to 20 carbon atoms, aryl of 6 to 20 carbon atoms, and aralkyl of 7 to 20 carbon atoms; and wherein $R^9$ is hydrogen or a linear or branched alkyl group of 1 to 20 carbon atoms;

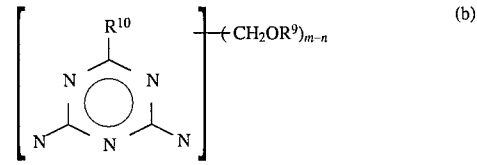

wherein $R^{10}$ is selected from the group consisting of alkyl of 1 to 20 carbon atoms, aryl of 6 to 20 carbon atoms, and aralkyl of 7 to 20 carbon atoms; and wherein $R^9$ is hydrogen or a linear or branched alkyl group of 1 to 20 carbon atoms;

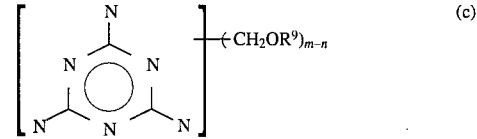

wherein $R^9$ is hydrogen or a linear or branched alkyl group of 1 to 20 carbon atoms, and provided the (c) is not N-alkyl substituted;

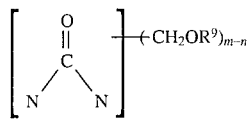
(d)

wherein
$R^9$ is hydrogen or a linear or branched alkyl group of 1 to 20 carbon atoms;

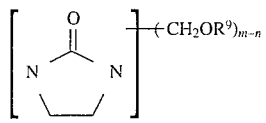
(e)

wherein
$R^9$ is hydrogen or a linear or branched alkyl group of 1 to 20 carbon atoms;

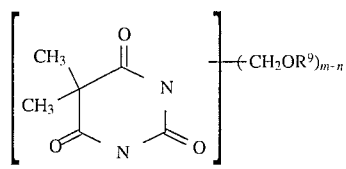
(f)

wherein
$R^9$ is hydrogen or a linear or branched alkyl group of 1 to 20 carbon atoms;

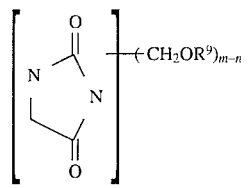
(g)

wherein
$R^9$ is hydrogen or a linear or branched alkyl group of 1 to 20 carbon atoms;

(h) oligomeric aminoplast anchor molecules derived from self- or cross-condensation of any of (a) through (g) and mixtures thereof; and (i) mixtures of any of (a) through (h).

3. The method as recited in claim 1, wherein the phenolic light stabilizer group is selected from the group consisting of 2-(2-hydroxyaryl)benzotriazoles, 2-hydroxybenzophenones, 2-(2-hydroxyaryl)-4,6-diaryl-1,3,5-triazines, salicylic acid derivatives, 2-hydroxyoxanilides, blocked derivatives thereof, and mixtures of any of the preceding light stabilizer groups.

4. The method as recited in claim 1, wherein A is attached through a methylene bridge replacing the $R^1$ or $R^5$ group on the phenolic ring.

5. The method as recited in claim 1, wherein A is attached through a methylene bridge replacing the $R^3$ group on the phenolic ring.

6. The method as recited in claim 2, wherein the phenolic light stabilizer group is selected from the group consisting of 2-(2-hydroxyaryl)benzotriazoles, 2-hydroxybenzophenones, 2-(2-hydroxyaryl)-4,6-diaryl-1,3,5-triazines, salicylic acid derivatives, 2-hydroxyoxanilides, blocked derivatives thereof, and mixtures of any of the preceding light stabilizer groups.

7. The method as recited in claim 2, wherein A is attached through a methylene bridge replacing the $R^1$ or $R^5$ group on the phenolic ring.

8. The method as recited in claim 2, wherein A is attached through a methylene bridge replacing the $R^3$ group on the phenolic ring.

9. The method as recited in claim 1, wherein the stabilizer composition comprises a monomeric or oligomeric aminoplast anchor having more than 0.5 mole of phenolic light stabilizer group per mole of aminoplast pendently attached thereto, represented by the formula

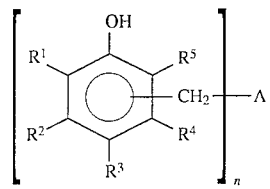

wherein
A is an m functional aminoplast anchor molecule to which n phenol rings are attached through n methylene bridges, said bridges replacing the $R^3$, $R^4$ or $R^5$ groups on the phenolic ring, which aminoplast anchor molecule is selected from the group consisting of

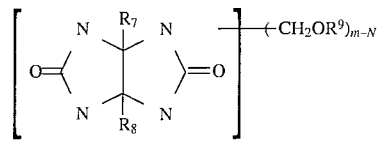
(a)

wherein
$R^7$ and $R^8$ are independently selected from the group consisting of hydrogen, alkyl of 1 to 20 carbon atoms, aryl of 6 to 20 carbon atoms, and aralkyl of 7 to 20 carbon atoms, and wherein
$R^9$ is hydrogen or a linear or branched alkyl group of 1 to 20 carbon atoms;

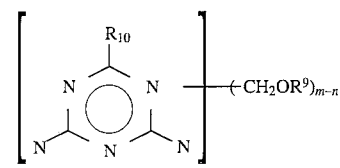
(b)

wherein
$R^{10}$ is selected from the group consisting of alkyl of 1 to 20 carbon atoms, aryl of 6 to 20 carbon atoms, and aralkyl of 7 to 20 carbon atoms, and wherein
$R^9$ is hydrogen or a linear or branched alkyl group of 1 to 20 carbon atoms;

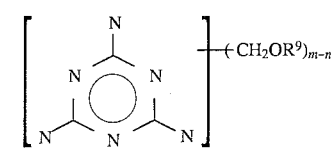
(c)

wherein
$R^9$ is hydrogen or a linear or branched alkyl group of 1 to 20 carbon atoms, and provided the (c) is not N-alkyl substituted;

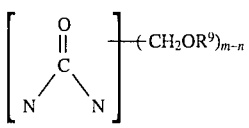

(d)

wherein
  $R^9$ is hydrogen or a linear or branched alkyl group of 1 to 20 carbon atoms;

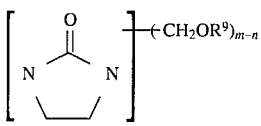

(e)

wherein
  $R^9$ is hydrogen or a linear or branched alkyl group of 1 to 20 carbon atoms;

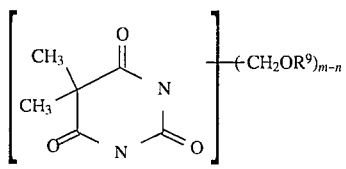

(f)

wherein
  $R^9$ is hydrogen or a linear or branched alkyl group of 1 to 20 carbon atoms;

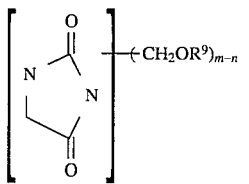

(g)

wherein
  $R^9$ is hydrogen or a linear or branched alkyl group of 1 to 20 carbon atoms;

(h) oligomeric aminoplast anchor molecules derived from self- or cross-condensation of any of (a) through (g) and mixtures thereof; and (i) mixtures of any of (a) through (h), wherein m is at least 1, and wherein n is more than 0.5, and wherein $R^1$ is selected from the group consisting of:

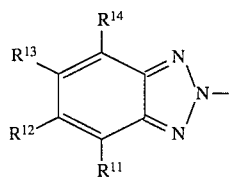

(j)

wherein
  each of $R^{11}$ through $R^{14}$ is independently selected from the group consisting of alkyl of 1 to 20 carbon atoms, alkoxy of 1 to 20 carbon atoms, aralkyl of 7 to 20 carbon atoms, hydrogen, chloro, bromo, cyano and nitro groups;

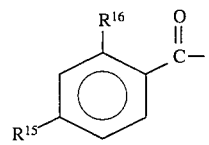

(k)

wherein
  each of $R^{15}$ and $R^{16}$ is independently selected from the group consisting of alkyl of 1 to 20 carbon atoms, alkoxy of 1 to 20 carbon atoms, aralkyl of 7 to 20 carbon atoms, hydrogen, chloro, bromo, cyano, nitro and hydroxy groups;

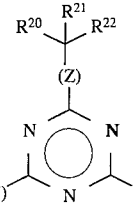

(l)

wherein Y and Z are the same or different aromatic carbocyclic radicals, and wherein each of $R^{17}$ through $R^{22}$ is independently selected from the group consisting of alkyl of 1 to 20 carbon atoms, alkoxy of 1 to 20 carbon atoms, hydrogen, chloro, bromo, cyano and nitro groups;

(m) carboxylic group or amides or esters thereof;

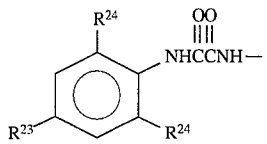

(n)

wherein each of $R^{23}$ and $R^{24}$ is independently selected from the group consisting of alkyl of 1 to 20 carbon atoms, alkoxy of 1 to 20 carbon atoms, aralkyl of 7 to 20 carbon atoms, hydrogen, chloro, bromo, cyano and nitro groups;

(o) mixtures of (j) to (n); and wherein $R^2$ is selected from the group consisting of hydrogen, alkyl of 1 to 20 carbon atoms, and aralkyl of 7 to 20 carbon atoms;

wherein $R^3$ is selected from the group consisting of hydrogen, alkyl of 1 to 20 carbon atoms, aralkyl of 7 to 20 carbon atoms, and alkyl of 1 to 20 carbon atoms which is interrupted, substituted, or interrupted and substituted by one or more oxygen, carbonyl or carboxy groups;

wherein $R^4$ is selected from the group consisting of hydrogen, hydroxy, alkyl of 1 to 20 carbon atoms, aralkyl of 7 to 20 carbon atoms, alkoxy of 1 to 20 carbon atoms, and alkyl of 1 to 20 carbon atoms which is interrupted, substituted, or interrupted and substituted by one or more oxygen, carbonyl or carboxy groups; and wherein $R^5$ is selected from the group consisting of hydrogen, alkyl of 1 to 20 carbon atoms, and aralkyl of 7 to 20 carbon atoms.

10. The method as recited in claim 9, wherein the stabilizer composition comprises a monomeric or oligomeric aminoplast anchor having more than 0.5 mole of phenolic light stabilizer group per mole of aminoplast pendently attached thereto, represented by the formula

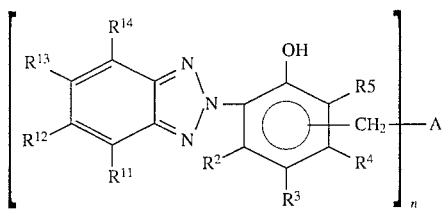

11. The method as recited in claim 10, wherein the aminoplast anchor is a group of the formula

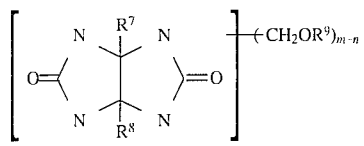 (a)

12. The method as recited in claim 10, wherein the aminoplast anchor is a group of the formula

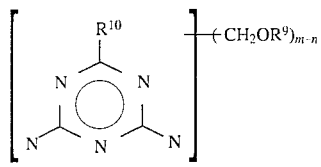 (b)

13. The method as recited in claim 10, wherein the aminoplast anchor is a group of the formula

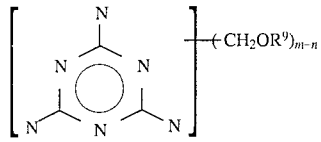 (c)

14. The method as recited in claim 10, wherein the aminoplast anchor is a group of the formula

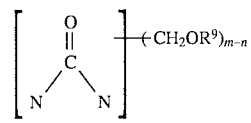 (d)

15. The method as recited in claim 10, wherein A is attached through a methylene bridge replacing the $R^5$ group on the phenolic ring.

16. The method as recited in claim 10, wherein A is attached through a methylene bridge replacing the $R^3$ group on the phenolic ring.

17. The method as recited in claim 9, wherein the stabilizer composition comprises a monomeric or oligomeric aminoplast anchor having more than 0.5 mole of phenolic light stabilizer group per mole of aminoplast pendently attached thereto, represented by the formula

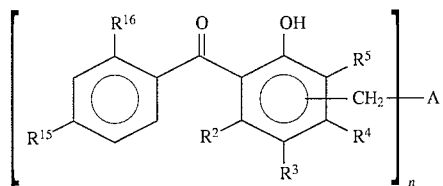

18. The method as recited in claim 17, wherein the aminoplast anchor is a group of the formula

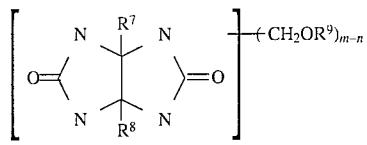 (a)

19. The method as recited in claim 17, wherein the aminoplast anchor is a group of the formula

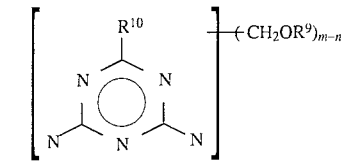 (b)

20. The method as recited in claim 17, wherein the aminoplast anchor is a group of the formula

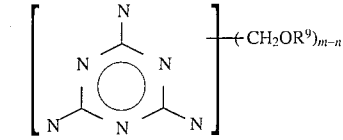 (c)

21. The method as recited in claim 17, wherein the aminoplast anchor is a group of the formula

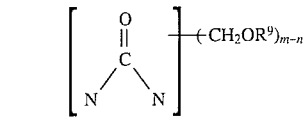 (d)

22. The method as recited in claim 17, wherein A is attached through a methylene bridge replacing the $R^5$ group on the phenolic ring.

23. The method as recited in claim 17, wherein A is attached through a methylene bridge replacing the $R^3$ group on the phenolic ring.

24. The method as recited in claim 9, wherein the stabilizer composition comprises a monomeric or oligomeric aminoplast anchor having more than 0.5 mole of phenolic light stabilizer group per mole of aminoplast pendently attached thereto, represented by the formula

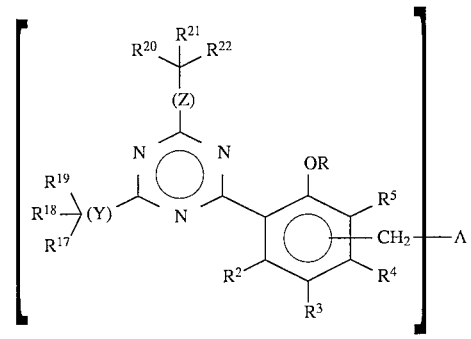

25. The method as recited in claim 24, wherein the aminoplast anchor is a group of the formula

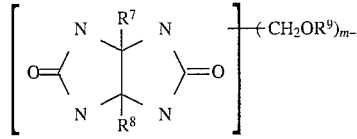 (a)

26. The method as recited in claim 24, wherein the aminoplast anchor is a group of the formula

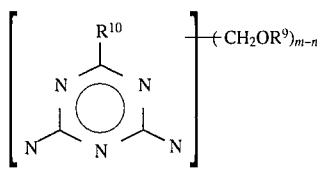
(b)

27. The method as recited in claim 24, wherein the aminoplast anchor is a group of the formula

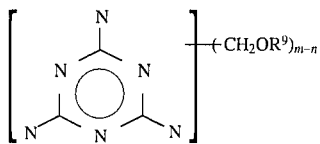
(c)

28. The method as recited in claim 24, wherein the aminoplast anchor is a group of the formula

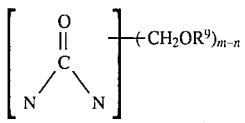
(d)

29. The method as recited in claim 24, wherein A is attached through a methylene bridge replacing the $R^5$ group on the phenolic ring.

30. The method as recited in claim 24, wherein A is attached through a methylene bridge replacing the $R^3$ group on the phenolic ring.

31. The method as recited in claim 9, wherein the stabilizer composition comprises a monomeric or oligomeric aminoplast anchor having more than 0.5 mole of phenolic light stabilizer group per mole of aminoplast pendently attached thereto, represented by the formula

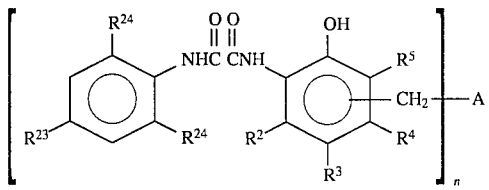

32. The method as recited in claim 31, wherein the aminoplast anchor is a group of the formula

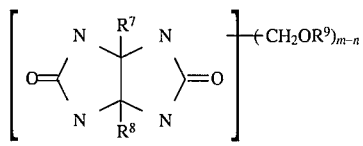
(a)

33. The method as recited in claim 31, wherein the aminoplast anchor is a group of the formula

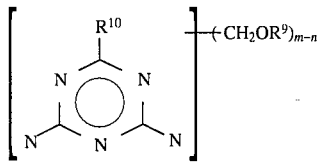
(b)

34. The method as recited in claim 31, wherein the aminoplast anchor is a group of the formula

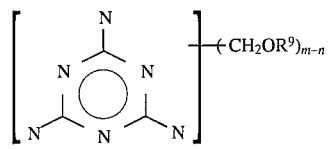
(c)

35. The method as recited in claim 31, wherein the aminoplast anchor is a group of the formula

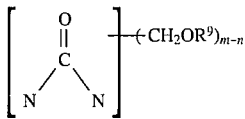
(d)

36. The method as recited in claim 31, wherein A is attached through a methylene bridge replacing the $R^5$ group on the phenolic ring.

37. The method as recited in claim 31, wherein A is attached through a methylene bridge replacing the $R^3$ group on the phenolic ring.

38. The method of claim 1, wherein the curable composition comprises (i) about 0.01 to 5 weight percent of the stabilizer composition, (ii) about 3 to 55 weight percent of the crosslinking agent, and (iii) about 40 to 97 weight percent of the polyfunctional active hydrogen containing material.

39. The method of claim 9, wherein the curable composition comprises (i) about 0.01 to 5 weight percent of the stabilizer composition, (ii) about 3 to 55 weight percent of the crosslinking agent, and (iii) about 40 to 97 weight percent of the polyfunctional active hydrogen containing material.

40. The method of claim 10, wherein the curable composition comprises (i) about 0.01 to 5 weight percent of the stabilizer composition, (ii) about 3 to 55 weight percent of the crosslinking agent, and (iii) about 40 to 97 weight percent of the polyfunctional active hydrogen containing material.

41. The method of claim 17, wherein the curable composition comprises (i) about 0.01 to 5 weight percent of the stabilizer composition, (ii) about 3 to 55 weight percent of the crosslinking agent, and (iii) about 40 to 97 weight percent of the polyfunctional active hydrogen containing material.

42. The method of claim 24, wherein the curable composition comprises (i) about 0.01 to 5 weight percent of the stabilizer composition, (ii) about 3 to 55 weight percent of the crosslinking agent, and (iii) about 40 to 97 weight percent of the polyfunctional active hydrogen containing material.

43. The method of claim 31, wherein the curable composition comprises (i) about 0.01 to 5 weight percent of the stabilizer composition, (ii) about 3 to 55 weight percent of the crosslinking agent, and (iii) about 40 to 97 weight percent of the polyfunctional active hydrogen containing material.

44. The method as recited in claim 1 wherein the crosslinking agent (ii) is an aminoplast resin selected from the group consisting of unetherified aminoplast resins, partially etherified aminoplast resins, fully etherified aminoplast resins, and mixtures thereof.

45. The method as recited in claim 44 wherein the aminoplast crosslinking agent is selected from the group consisting of alkoxymethylated melamines, alkoxymethylated guanamines, alkoxymethylated glycolurils, alkoxymethylated ureas, oligomers thereof, and mixtures of any of the preceding crosslinking agents.

46. The method as recited in claim 1 wherein the polyfunctional active hydrogen containing material (iii) comprises at least one class of active hydrogen functionality selected from the group consisting of hydroxy, mercapto, amido, carboxy, and a group convertible thereto.

47. The method as recited in claim 46 wherein the active hydrogen containing material (iii) is selected from the group consisting of acrylic resins, polyester resins, polyurethane polyols, products of condensation of amines with epoxy resins, polyols, polycarboxy compounds, polymercaptans, polyamides, and mixtures thereof.

48. The method as recited in claim 1 further comprising a cure catalyst (iv).

49. The method as recited in claim 48 wherein the cure catalyst is selected from the group consisting of sulfonic acids, carboxylic acids, phosphonic acids, sulfonimides, nitric acid, sulfuric acid, and phosphoric acid.

50. The method as recited in claim 49 wherein the cure catalyst is selected from the group consisting of para-toluenesulfonic acid, benzenesulfonic acid, dinonylnaphthalenedisulfonic acid, naphthalenesulfonic acid, dodecylbenzenesulfonic acid, and methyl para-tolylsulfonimide.

51. The method as recited in claim 50 wherein the cure catalyst is para-toluenesulfonic acid.

52. The method as recited in claim 1 wherein the substrate is selected from the group consisting of steel, aluminum, and plastic materials.

53. The method as recited in claim 1 wherein contacting is carried out by a method selected from the group consisting of spraying, padding, brushing, electrostatic spraying, roller coating, curtain coating, flow coating, dipping, and electrocoating.

54. The method as recited in claim 1 wherein the curing is carried out by continued application of heat.

* * * * *

UNITED STATES PATENT AND TRADEMARK OFFICE
CERTIFICATE OF CORRECTION

PATENT NO. : 5,612,084

DATED : March 18, 1997

INVENTOR(S) : Jeno G. Szita and Paul S. Waterman

It is certified that error appears in the above-identified patent and that said Letters Patent is hereby corrected as shown below:

Column 52, structure (a), change "m-N" to --m-n--.

(a)
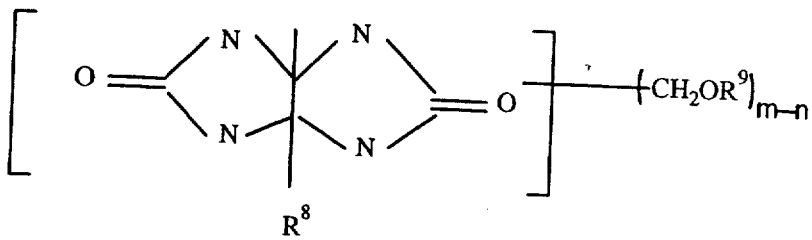

UNITED STATES PATENT AND TRADEMARK OFFICE
CERTIFICATE OF CORRECTION

PATENT NO. : 5,612,084
DATED : March 18, 1997
INVENTOR(S) : Jeno G. Szita and Paul S. Waterman It is certified that error appears in the above-identified patent and that said Letters Patent is hereby corrected as shown below:

Column 54, structure (I), change "$R^{16}$" to --$R^{18}$--.

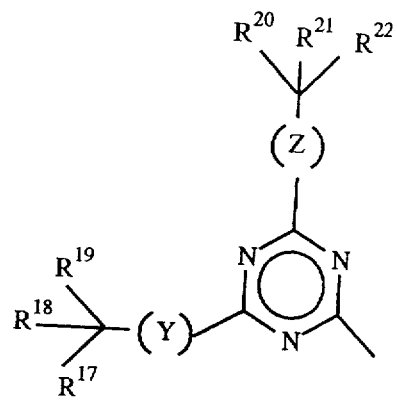

Signed and Sealed this

Sixth Day of January, 1998

Attest:

BRUCE LEHMAN

Attesting Officer    Commissioner of Patents and Trademarks